United States Patent
Peng et al.

(10) Patent No.: US 7,138,491 B2
(45) Date of Patent: Nov. 21, 2006

(54) CARBOLINE-3-CARBOXYLIC ACID MODIFIED RELATED SEQUENCES OF ALA-ARG-PRO-ALA-LYS, THEIR SYNTHESIS AND USE AS THROMOBOLYTIC AGENT

(75) Inventors: Shiqi Peng, Beijing (CN); Ming Zhao, Beijing (CN); Chao Wang, Beijing (CN); Yangfen Wu, Beijing (CN)

(73) Assignee: Guangzhou Bai Yun Shan Pharmaceutical Co., Ltd. (CN)

( * ) Notice: Subject to any disclaimer, the term of this patent is extended or adjusted under 35 U.S.C. 154(b) by 0 days.

(21) Appl. No.: 10/680,293

(22) Filed: Oct. 8, 2003

(65) Prior Publication Data

US 2005/0080015 A1   Apr. 14, 2005

(51) Int. Cl.
*A61K 38/00*   (2006.01)
(52) U.S. Cl. ...................................... 530/345
(58) Field of Classification Search ............... 514/2
See application file for complete search history.

(56) References Cited

FOREIGN PATENT DOCUMENTS

CN           1373139          * 10/2002

OTHER PUBLICATIONS

Wu et al, Synthesis and Thrombolytic Activity of Pseudopeptides Related to Fibrinogen Fragment, Bioorganic & Medicinal Chemistry Letters, vol. 12 Sep. (2002), pp. 2331-2333.*
Wu Y, Zhao M, Wang C, Peng S Synthesis and thrombolytic activity of pseudopeptides related to fibrinogen fragment.Bioorg Med Chem Lett. Sep. 2, 2002; 12(17):2331-3.*

* cited by examiner

*Primary Examiner*—Cecilia J. Tsang
*Assistant Examiner*—Thomas S. Heard
(74) *Attorney, Agent, or Firm*—Finnegan, Henderson, Farabow, Garrett & Dunner, LLP

(57) ABSTRACT

The present invention relates to the protected intermediates and the deprotected products of P6A, related to the protected pseudopeptides introducing the protected intermediateds of P6A to 3S-(2-Boc)-1,2,3,4-tetrahydro-β-carboline-3-carboxylic acid and the deprotected pseudopeptides, related to the protected pseudopeptides introducing the protected intermediateds of P6A to 3S-1,2,3,4-tetrahydro-β-carboline-3-carboxylic acid benzyl ester, related to the methods for their preparation, and related to their use as the thrombolytic agents.

6 Claims, No Drawings

CARBOLINE-3-CARBOXYLIC ACID MODIFIED RELATED SEQUENCES OF ALA-ARG-PRO-ALA-LYS, THEIR SYNTHESIS AND USE AS THROMOBOLYTIC AGENT

FIELD OF THE INVENTION

The present invention relates to the protective intermediates and the deprotective products of the related sequences of Ala-Arg-Pro-Ala-Lys (SEQ ID NO: 1) (P6A), related to coupling the protective intermediates of C-terminal or N-terminal free with carboline-3-carboxylic acid to form the corresponding protective pseudopeptides which were then deprotected to form the corresponding deprotective pseudopeptides, related to the methods for their preparation, and further related to their use as medicine especially as thrombolytic agent

BACKGROUND OF THE INVENTION

P6A (H-Ala-Arg-Pro-Ala-Lys-OH) (SEQ ID NO: 1), one of the products obtained from the degradation of fibrinogen, was used as the lead compound in our previous studies on thrombolysis agents (Zhao, M.; Peng, S. Q. J Prakt. Chem. 1999, 341, 668; Zhao, M.; Lin, N.; Wang, C.; Peng, S. Q. Bioorg Med Chem Lett. 2003, 13, 961). As essential part of the researches the metabolism of P6A arouses our interest. In the identification of the in vivo metabolites the solution of P6A in normal saline was injected into the tail vein of the mice. After 20 min the plasma was isolated from the whole blood of the mice. To the plasma perchloric acid was added in order to free all of the metabolites of P6A from the plasma protein, centrifuged to separate the upper layer as a clear solution, and injected into the HPLC column of the HPLC/ESI/MS. In the HPLC/ESI/MS analysis all the possible ions of the metabolites from P6A in vivo were monitored by ESI/MS. According to the trapped ions the corresponding sequences were H-Ala-Arg-Pro-Ala-OH (SEQ ID NO: 2) (FAB/MS, 414), H-Ala-Arg-Pro-OH (FAB/MS, 343), H-Arg-Pro-Ala-Lys-OH (SEQ ID NO: 3) (FAB/MS, 471), and H-Pro-Ala-Lys-OH (FAB/MS, 315). In the isolation of the in vitro metabolite P6A was added to the mice blood directly, incubated at 37° C. for 20 min, and centrifuged at 0° C. to isolate the plasma. To the plasma perchloric acid was added to free all of the metabolites of P6A from the plasma protein, and centrifuged to separate the upper layer which was frozen and lyophilized. The resulted crystals were dissolved in water and injected into the column. The fractions corresponding to the main peaks were collected, frozen and lyophilized. The FAB/MS tests of the resulted 4 crystals gave the same sequences as that as mentioned above.

The euglobulin clot lysis activity of the isolated metabolites resulted from the in vitro assay indicated that for development of thrombolytic peptides the corresponding modifications may be interesting. In the previous modification of oligopeptides we demonstrated that the introduction of 3S-1,2,3,4-tetrahydro-β-carboline-3-carboxylic acid may result in enhancement of bioactivity (Lin, N.; Zhao, M.; Wang, C.; Peng, S. Q. Bioorg Med Chem Lett. 2002, 12, 585; WU, Y. F.; Zhao, M.; Wang, C.; Peng, S. Q. Bioorg Med Chem Lett. 2002, 12, 2331).

In the present invention the pseudopeptides consisted of 3S-1,2,3,4-tetrahydro-β-carboline-3-carboxylic acid, which was prepared according to Scheme 1, H-Ala-Arg-Pro-Ala-Lys-OH (SEQ ID NO: 1), H-Gln-Arg-Pro-Ala-Lys-OH (SEQ ID NO: 4), H-Lys-Arg-Pro-Ala-Lys-OH (SEQ ID NO: 5), H-Asn-Arg-Pro-Ala-Lys-OH (SEQ ID NO: 6), H-Ala-Arg-Pro-Ala-Lys-OH (SEQ ID NO: 1), H-Ala-Arg-Pro-Ala-OH (SEQ ID NO: 2), H-Ala-Arg-Pro-OH, H-Arg-Pro-Ala-Lys-OH (SEQ ID NO: 3) and H-Pro-Ala-Lys-OH, which were prepared according to Scheme 2, were prepared. The thrombolitic activities of the pseudopeptides were observed in vitro and in vivo.

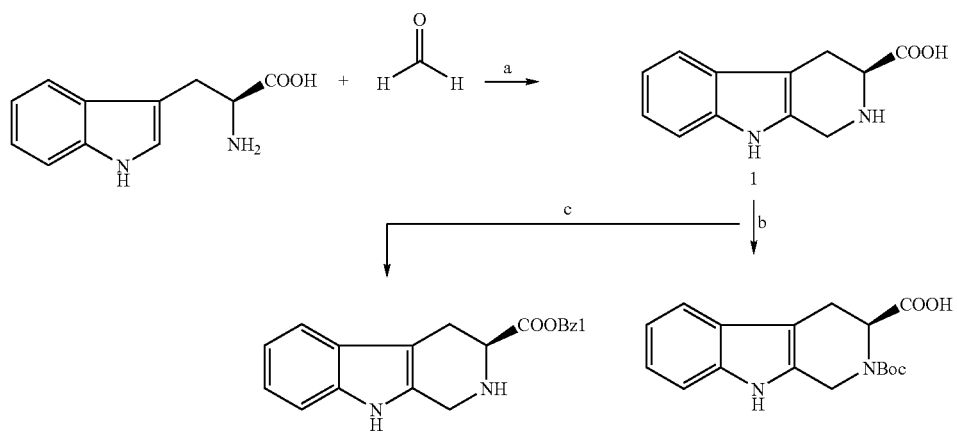

Scheme 1. Synthesis, esterification and acylation of 3S-1,2,3,4-tetrahydro-β-carboline-3-carboxylic acid, 3S-(2-Boc)-1,2,3,4-tetrahydro-β-carboline-3-carboxylic acid and 3S-1,2,3,4-tetrahydro-β-carboline-3-carboxylic acid benzyl ester. (a) sulfuric acid; (b) (BOC)$_2$O; (c) Cs$_2$CO$_3$, C$_6$H$_5$CH$_2$Br.

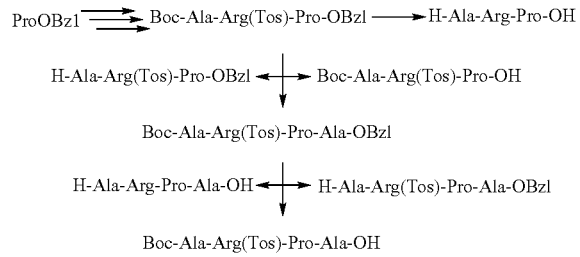

According to the synthetic route depicted in Scheme 3 the compounds of Boc-AA$_1$-AA$_2$-Pro-AA$_3$-AA$_4$-OBzl(1) in the present invention, wherein AA$_1$ represented Ala, AA$_2$ represented Arg(Tos), AA$_3$ and AA$_4$ together represented Ala; or AA$_1$ represented Ala, AA$_2$, AA$_3$ and AA$_4$ together represented Arg(Tos); or AA$_1$ and AA$_2$ together represented Arg(Tos), AA$_3$ represented Ala, AA$_4$ represented Lys(ClZ).

According to the synthetic route depicted in FIG. 2 the compounds of H-AA$_1$-AA$_2$-Pro-AA$_3$-AA$_4$-OH (2) in the present invention, wherein AA$_1$ represented Ala, Gly, Gln, Lys, Asn, AA$_2$ represented Arg, AA$_3$ represented Ala, AA$_4$ represented Lys or AA$_1$ represented Ala, AA$_2$ represented Arg, AA$_3$ and AA$_4$ together represented Ala; or AA$_1$ represented Ala, AA$_2$, AA$_3$ and AA$_4$ together represented Arg; or AA$_1$ and AA$_2$ together represented Arg, AA$_3$ represented Ala, AA$_4$ represented Lys, were deprotected with HF and the formed products were used for bioassay as control.

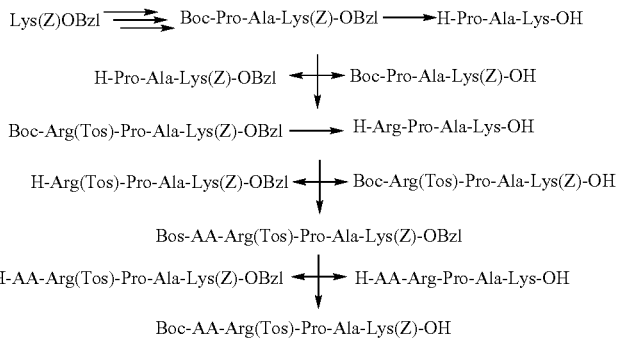

Scheme 3. Synthetic route for Boc-Ala-Arg(Tos)-Pro-Ala-OBzl (SEQ ID NO: 7), Boc-Ala-Arg(Tos)-Pro-OBzl, H-Ala-Arg-Pro-Ala-OH (SEQ ID NO: 2) and H-Ala-Arc,-Pro-OH. (Sequences shown above are SEQ ID NOS 7, 2, 7 and 7, respectively in order of appearance).

Scheme 2. Synthetic route for related sequences of H-AA-Arg-Pro-Ala-Lys-OH (SEQ ID NO: 10), H-Arg-Pro-Ala-Lys-OH (SEQ ID NO: 3) and H-Pro-Ala-Lys-OH. Wherein AA=Ala, Gly, Asn, Arg(Tos), Lys(Z), Arg, or Lys. (Sequences shown above are SEQ ID NOS 8, 3, 8, 8, 9, 9, 10 and 9, respectively in order of appearance).

SUMMARY OF THE INVENTION

The present invention relates to the protective intermediates and the deprotective products of the related sequences of Ala-Arg-Pro-Ala-Lys (SEQ ID NO: 1) (P6A), related to coupling the protective intermediates of C-terminal or N-terminal free with carboline-3-carboxylic acid to form the corresponding protective pseudopeptides which were then deprotected to form the corresponding deprotective pseudopeptides, related to the methods for their preparation, and further related to their use as medicine especially as thrombolytic agent.

According to the synthetic route depicted in Scheme 2 the compounds of Boc-AA$_1$-AA$_2$-Pro-AA$_3$-AA$_4$-OBzl(1) (SEQ ID NO: 11) in the present invention, wherein AA$_1$ represented Ala, Gly, Gln, Lys(ClZ) or Asn, AA$_2$ represented Arg(Tos), AA$_3$ represented Ala, AA$_4$ represented Lys(ClZ), were prepared by use of the solution method.

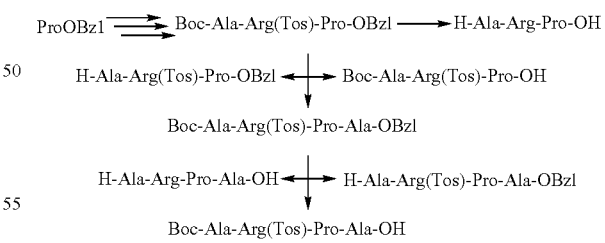

Scheme 3. Synthetic route for related sequences of H-Ala-Arg-Pro-Ala-OH (SEQ ID NO: 2) and H-Ala-Arg-Pro-OH. (Sequences shown above are SEQ ID NOS 7, 2, 7 and 7, respectively in order of appearance).

Treating the compounds of formular (1) with the solution of hydrogen chloride in ethyl acetate (6 mol/L) their Boc group was removed and the compounds of H-AA$_1$-AA$_2$-Pro-AA$_3$-AA$_4$-OBzl(3), wherein AA$_1$ represented Ala, Gly, Gln, Lys(ClZ), or Asn, $AA_2$ represented Arg(Tos), $AA_3$ represented Ala, $AA_4$ represented Lys(ClZ); or $AA_1$ represented Ala, $AA_2$ represented Arg(Tos), $AA_3$ and $AA_4$ together represented Ala; or $AA_1$ represented Ala, $AA_2$, $AA_3$ and $AA_4$ together represented Arg(Tos); or $AA_1$ and $AA_2$ together represented Arg(Tos), $AA_3$ represented Ala, $AA_4$ represented Lys(ClZ), were obtained.

Treating the compounds of formular (1) with the solution of sodium hydroxide in methanol (2 mol/L) their ester group was removed and the compounds of Boc-$AA_1$-$AA_2$-Pro-$AA_3$-$AA_4$-OH(4), wherein $AA_1$ represented Ala, Gly, Gln, Lys(ClZ), or Asn, $AA_2$ represented Arg(Tos), $AA_3$ represented Ala, $AA_4$ represented Lys(ClZ); or $AA_1$ represented Ala, $AA_2$ represented Arg(Tos), $AA_3$ and $AA_4$ together represented Ala; or $AA_1$ represented Ala, $AA_2$, $AA_3$ and $AA_4$ together represented Arg(Tos); or $AA_1$ and $AA_2$ together represented Arg(Tos), $AA_3$ represented Ala, $AA_4$ represented Lys(ClZ), were obtained.

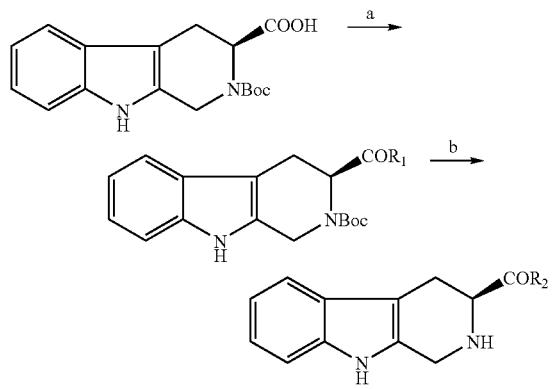

Scheme 4. Synthetic route for N-3S-1,2,3,4-tetrahydro-β-carboline-3-carboxyl-oligopeptides dicyclohexylcarbodiimide, N-methylmorpholine, and H-Arg(Tos)-Pro-Ala-Lys(Z)-OBzl·HCl (SEQ ID NO: 8), or H-Pro-Ala-Lys(Z)-OBzl.HCl, or H-Ala-Arg(Tos)-Pro-Ala-OBzl.HCl (SEQ ID NO: 7), or H-Ala-Arg(Tos)-Pro-OBzl.HCl; b) HF; in 4a, $R_1$=-Arg(Tos)-Pro-Ala-Lys(Z)-OBzl (SEQ ID NO: 8); in 4b, $R_1$=-Pro-Ala-Lys(Z)-OBzl; in 4c, $R_1$=-Ala-Arg(Tos)-Pro-Ala-OBzl (SEQ ID NO: 7); in 4d, $R_1$=-Ala-Arg(Tos)-Pro-OBzl; in 5a, $R_2$=-Arg-Pro-Ala-Lys-OH (SEQ ID NO: 3); in 5b, $R_2$=-Pro-Ala-Lys-OH; in 5c, $R_2$=-Ala-Arg-Pro-Ala-OH (SEQ ID NO: 2); in 5d, $R_2$=-Ala-Arg-Pro-OH.

According to the synthetic rout depicted in Scheme 4 the compounds of formular 3, wherein $AA_1$ represented Ala, Gly, Gln, Lys (ClZ) or Asn, $AA_2$ represented Arg(Tos), $AA_3$ represented Ala, $AA_4$ represented Lys(ClZ) or $AA_1$ represented Ala, $AA_2$ represented Arg(Tos), $AA_3$ and $AA_4$ together represented Ala; or $AA_1$ represented Ala, $AA_2$, $AA_3$ and $AA_4$ together represented Arg(Tos); or $AA_1$ and $AA_2$ together represented Arg(Tos), $AA_3$ represented Ala, $AA_4$ represented Lys(ClZ), were coupled with 3S-(2-Boc)-1,2,3,4-tetrahydro-β-carboline-3-carboxylic acid to provide the compounds of $R_1$-$AA_1$-$AA_2$-Pro-$AA_3$-$AA_4$-$R_2$(5), wherein $R_1$ represented 3S-(2-Boc)-1,2,3,4-tetrahydro-β-carboxyl, $AA_1$ represented Ala, Gly, Gln, Lys(ClZ) or Asn, $AA_2$ represented Arg(Tos), $AA_3$ represented Ala, $AA_4$ represented Lys(ClZ), $R_2$ represented OBzl; or $R_1$ represented 3S-(2-Boc)-1,2,3,4-tetrahydro-β-carboline-3-carboxyl, $AA_1$ represented Ala, $AA_2$ represented Arg(Tos), $AA_3$, $AA_4$ and $R_2$ together represented Ala-OBzl; or $R_1$ represented 3S-(2-Boc)-1,2,3,4-tetrahydro-β-carboline-3-carboxyl, $AA_1$ represented Ala, $AA_2$ represented Arg(Tos), $AA_3$, $AA_4$ and $R_2$ together represented OBzl; or $R_1$ represented 3S-(2-Boc)-1,2,3,4-tetrahydro-β-carboline-3-carboxyl, $AA_1$ and $AA_2$ together represented Arg(Tos), $AA_3$ represented Ala, $AA_4$ represented Lys(ClZ), $R_2$ represented OBzl; or $R_1$ represented 3S-(2-Boc)-1,2,3,4-tetrahydro-β-carboline-3-carboxyl, $AA_1$, $AA_2$ and $AA_3$ together represented H, $AA_3$ represented Ala, $AA_4$ represented Lys(ClZ), $R_2$ represented OBzl. The compounds of formular 5 were deprotected with HF to provide the compounds of $R_1$-$AA_1$-$AA_2$-Pro-$AA_3$-$AA_4$-$R_2$(5), wherein $R_1$ represented 3S-(2-Boc)-1,2,3,4-tetrahydro-β-carboline-3-carboxyl, $AA_1$ represented Ala, Gly, Gln, Lys or Asn, $AA_2$ represented Arg, $AA_3$ represented Ala, $AA_4$ and $R_2$ together represented Lys-OH; or $R_1$ represented 3S-(2-Boc)-1,2,3,4-tetrahydro-β-carboline-3-carboxyl, $AA_1$ represented Ala, $AA_2$ represented Arg, $AA_3$, $AA_4$ and $R_2$ together represented Ala-OH; or $R_1$ represented 3S-(2-Boc)-1,2,3,4-tetrahydro-β-carboline-3-carboxyl, $AA_1$ represented Ala, $AA_2$ represented Arg, $AA_3$, $AA_4$ and $R_2$ together represented OH; or $R_1$ represented 3S-(2-Boc)-1,2,3,4-tetrahydro-β-carboline-3-carboxyl, $AA_1$ and $AA_2$ together represented Arg, $AA_3$ represented Ala, $AA_4$ and $R_2$ together represented Lys-OH; or $R_1$ represented 3S-(2-Boc)-1,2,3,4-tetrahydro-β-carboline-3-carboxyl, $AA_1$ and $AA_2$ together represented H, $AA_3$ represented Ala, $AA_4$ and $R_2$ together represented Lys-OH.

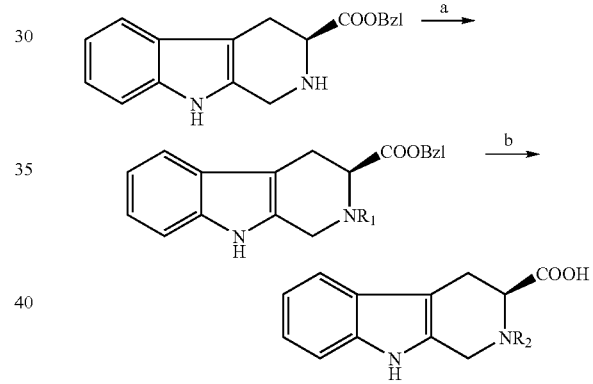

Scheme 5. Synthetic route for 3S-2-oligopeptidyl-1,2,3,4-tetrahydro-β-carboline-3-carboxylic acids. a) dicyclohexylcarbodiimide, N-methylmorpholine, and Boc-Arg(Tos)-Pro-Ala-Lys(Z)-OH (SEQ ID NO: 8), or Boc-Pro-Ala-Lys(Z)-OHl, or Boc-Ala-Arg(Tos)-Pro-Ala-OH (SEQ ID NO: 7), or Boc-Ala-Arg(Tos)-Pro-OH; b) HF; in 6a, $R_1$=H-Arg(Tos)-Pro-Ala-Lys(Z)- (SEQ ID NO: 8); in 6b, $R_1$=H-Pro-Ala-Lys(Z)-; in 6c, $R_1$=H-Ala-Arg(Tos)-Pro-Ala-(SEQ ID NO: 7); in 6d, $R_1$=H-Ala-Arg(Tos)-Pro-; in 7a, $R_2$=H-Arg-Pro-Ala-Lys-(SEQ ID NO: 3); in 7b, $R_2$=H-Pro-Ala-Lys-; in 7c, $R_2$=H-Ala-Arg-Pro-Ala- (SEQ ID NO: 2); in 7d, $R_2$=H-Ala-Arg-Pro-.

According to the synthetic rout depicted in Scheme 5 the compounds of formular 4, wherein $AA_1$ represented Ala, Gly, Gln, Lys(ClZ) or Asn, $AA_2$ represented Arg(Tos), $AA_3$ represented Ala, $AA_4$ represented Lys(ClZ) or $AA_1$ represented Ala, $AA_2$ represented Arg(Tos), $AA_3$ and $AA_4$ together represented Ala; or $AA_1$ represented Ala, $AA_2$, $AA_3$ and $AA_4$ together represented Arg(Tos); or $AA_1$ and $AA_2$ together represented Arg(Tos), $AA_3$ represented Ala, $AA_4$ represented Lys(ClZ), were coupled with 3S-1,2,3,4-tetrahydro-β-carboline-3-carboxylic acid benzyl ester to provide the compounds of $R_1$-$AA_1$-$AA_2$-Pro-$AA_3$-$AA_4$-$R_2$(5), wherein $R_1$ represented Boc, $AA_1$ represented Ala, Gly, Gln, Lys(ClZ) or Asn, $AA_2$ represented Arg(Tos), $AA_3$ represented Ala, $AA_4$ represented Lys(ClZ), $R_2$ represented 3S-1,2,3,4-tetrahydro-β-carboline-3-carboxylic acid benzyl ester-2-yl; or $R_1$ represented Boc, $AA_1$ represented Ala, $AA_2$ represented Arg(Tos), $AA_3$ represented Ala, $AA_4$ and $R_2$ together represented 3S-1,2,3,4-tetrahydro-β-carboline-3-carboxylic acid benzyl ester-2-yl; or $R_1$ represented Boc, $AA_1$ represented Ala, $AA_2$ represented Arg(Tos), $AA_3$, $AA_4$ and $R_2$ together represented 3S-1,2,3,4-tetrahydro-β-carboline-3-carboxylic acid benzyl ester-2-yl; or $R_1$ represented Boc, $AA_1$ and $AA_2$ together represented Arg(Tos), $AA_3$ represented Ala, $AA_4$ represented Lys(ClZ), $R_2$ represented 3S-1,2,3,4-tetrahydro-β-carboline-3-carboxylic acid benzyl ester-2-yl; or $R_1$ represented Boc, $AA_1$ and $AA_2$ together represented H, $AA_3$ represented Ala, $AA_4$ represented Lys (ClZ), $R_2$ represented 3S-1,2,3,4-tetrahydro-β-carboline-3-carboxylic acid benzyl ester-2-yl. The coupled products were deprotected with HF to form the deprotected products of $R_1$-$AA_1$-$AA_2$-Pro-$AA_3$-$AA_4$-$R_2$(5), wherein $R_1$ and $AA_1$ together represented Ala, Gly, Gln, Lys or Asn, $AA_2$ represented Arg, $AA_3$ represented Ala, $AA_4$ represented Lys, $R_2$ represented 3S-1,2,3,4-tetrahydro-β-carboline-3-carboxylic acid-2-yl; or $R_1$ and $AA_1$ together represented Ala, $AA_2$ represented Arg, $AA_3$ represented Ala, $AA_4$ and $R_2$ together represented 3S-1,2,3,4-tetrahydro-β-carboline-3-carboxylic acid-2-yl; or $R_1$ and $AA_1$ together represented Ala, $AA_2$ represented Arg, $AA_3$ represented Ala, $AA_4$ and $R_2$ together represented 3S-1,2,3,4-tetrahydro-β-carboline-3-carboxylic acid-2-yl; or $R_1$, $AA_1$ and $AA_2$ together represented Arg, $AA_3$ represented Ala, $AA_4$ represented Lys, $R_2$ represented 3S-1,2,3,4-tetrahydro-β-carboline-3-carboxylic acid-2-yl; or $R_1$, $AA_1$ and $AA_2$ together represented H, $AA_3$ represented Ala, $AA_4$ represented Lys, $R_2$ represented 3S-1,2,3,4-tetrahydro-β-carboline-3-carboxylic acid-2-yl.

In the present invention the thrombolytic activities of the compounds of formular 5, wherin $R_1$ represented 3S-(2-Boc)-1,2,3,4-tetrahydro-β-carboline-3-carboxyl, $AA_1$ represented Ala, Gly, Gln, Lys or Asn, $AA_2$ represented Arg, $AA_3$ represented Ala, $AA_4$ and $R_2$ together represented Lys-OH; or $R_1$ represented 3S-(2-Boc)-1.2,3,4-tetrahydro-β-carboline-3-carboxyl, $AA_1$ represented Ala, $AA_2$ represented Arg, $AA_3$, $AA_4$ and $R_2$ together represented Ala-OH; or $R_1$ represented 3S-(2-Boc)-1,2,3,4-tetrahydro-β-carboline-3-carboxyl, $AA_1$ represented Ala, $AA_2$ represented Arg, $AA_3$, $AA_4$ and $R_2$ together represented OH; or $R_1$ represented 3S-(2-Boc)-1,2,3,4-tetrahydro-β-carboline-3-carboxyl, $AA_1$ and $AA_2$ together represented Arg, $AA_3$ represented Ala, $AA_4$ and $R_2$ together represented Lys-OH; or $R_1$ represented 3S-(2-Boc)-1,2,3,4-tetrahydro-β-carboline-3-carboxyl, $AA_1$ and $AA_2$ together represented H, $AA_3$ represented Ala, $AA_4$ and $R_2$ together represented Lys-OH; or $R_1$ and $AA_1$ together represented Ala, Gly, Gln, Lys or Asn, $AA_2$ represented Arg, $AA_3$ represented Ala, $AA_4$ represented Lys, $R_2$ represented 3S-1,2,3,4-tetrahydro-β-carboline-3-carboxylic acid-2-yl; or $R_1$ and $AA_1$ together represented Ala, $AA_2$ represented Arg, $AA_3$ represented Ala, $AA_4$ and $R_2$ together represented 3S-1,2,3,4-tetrahydro-β-carboline-3-carboxylic acid-2-yl; or $R_1$ and $AA_1$ together represented Ala, $AA_2$ represented Arg, $AA_3$ represented Ala, $AA_4$ and $R_2$ together represented 3S-1,2,3,4-tetrahydro-β-carboline-3-carboxylic acid-2-yl; or $R_1$, $AA_1$ and $AA_2$ together represented Arg, $AA_3$ represented Ala, $AA_4$ represented Lys, $R_2$ represented 3S-1,2,3,4-tetrahydro-β-carboline-3-carboxylic acid-2-yl; or $R_1$, $AA_1$ and $AA_2$ together represented H, $AA_3$ represented Ala, $AA_4$ represented Lys, $R_2$ represented 3S-1,2,3,4-tetrahydro-β-carboline-3-carboxylic acid-2-yl, were assaied. It was found that the pseudopeptides mentioned exhibited significant and dose-dependent thrombolytic activity.

DETAILED DESCRIPTION OF THE EMBODIMENTS

The present invention is described in detail with reference to the following examples. These examples, however, are intended to illustrate the present invention and should not be construed as limiting the scope of the present invention.

General The protected amino acids with L-configuration, used in this work, were purchased from Sigma Chemical Co (USA). All of the coupling and deprotective reactions were carried out under anhydrous conditions. Chromatography was performed on Qingdao silica gel H (Qingdao of China). The purities of the intermediates and the products were confirmed by TLC (Merck silica gel plates of type 60 $F_{254}$, 0.25 mm layer thickness, Germany) and HPLC (Waters, $C_{18}$ column 4.6×150 mm, USA). The amino acid analysis was determined with a Hitachi 835-50 instrument (Japan). FAB-MS was determined by VG-ZAB-MS (UK), high resolution GC/MS/DS (UK) and HP ES-5989x (USA). Optical rotations were determined with a Schmidt+Haensch Polartromic D instrument (Germany). The statistical analysis of all the biological date was carried out by use of ANOVA test, $p<0.05$ is considered significant.

EXAMPLE 1

The preparation of 3S-1,2,3,4-tetrahydro-β-carboline-3-carbo-xylic acid

To the mixture of 5.0 g (24.5 mmol) of L-tryptophan, 25 ml of $H_2SO_4$ (1 mol/L) and 80 ml of water 8 ml of formaldehyde (36–38%) were added. The reaction mixture was stirred at room temperature for 2 h and adjusted to pH 6–7 with concentrated ammonia aqueous. The mixture obtained was kept at 0° C. for 12 h and the formed precipitates were collected by filtration. After recrystallization 3.97 g (75%) of the title compound were obtained as a colorless powder. mp. 280–282° C.; EI/MS: 217 [M+H]$^+$; $^1$H NMR (BHSC-500, DMSO-$d_6$): δ=12.80(s, 1H), 10.99(s, 1H), 7.44(d, J=7.5 Hz, 1H), 7.33(t, J=8.0 Hz, 1H) 17.08(t, J=8.0 Hz, 1H), 6.99(t, J=7.5 Hz, 1H), 4.22(d, J=4.8 Hz, H), 3.69(dd, J=10.5 Hz, J=5.0 Hz, 1H), 3.14(dd, J=10.5 Hz, J=2.4 Hz, 1H), 2.83(ddd, J=10.5 Hz, J=5.0 Hz, J=2.4 Hz, 2H), 2.80(s, 1H).

EXAMPLE 2

The preparation of N-Boc-3S-1,2,3,4-tetrahydro-β-carboline-3-carboxylic acid

The suspension of 1.1 g (5.0 mmol) of 3S-1,2,3,4-tetrahydro-β-carboline-3-carboxylic acid in 15 ml of N,N-dimethylformamide and 1.4 ml of triethylamine was vigorously stirred at room temperature, to which 1.1 g (7.7 mmol) of Boc-$N_3$ was added in 30 min. The reaction mixture was stirred at room temperature for 24 h and at 40° C. for 80 h. To the reaction mixture 5 ml of citric acid in water (20%) were added and the solution was extracted with ethyl acetate (30 ml×3). The separated ethyl acetate layer was dried with anhydrous $MgSO_4$. After removal of $MgSO_4$ by filtration the filtrate was evaporated to dryness. The residue obtained was crystallized in $CHCl_3$ to give 1.20 g (76%) of the title compound. mp. 165–170° C.; TOF/MS: 317 [M+H]$^+$, 339 [M+Na]$^+$, 355[M+K]; $^1$H NMR (BHSC-500, DMSO-$d_6$):

δ=12.77(s, 1H), 10.87(s, 1H), 6.92–7.41 (m, 4H), 5.02–5.14 (m, 1H), 4.29–4.75 (m, 2H), 3.25–3.34 (m, 2H), 1.46(s, 9H).

EXAMPLE 3

The preparation of 3S-1,2,3,4-tetrahydro-β-carboline-3-carboxylic acid benzyl ester The solution of 280 mg (0.86 mmol) of $Cs_2CO_3$ in 1 ml of water was mixed with the solution of 540 mg (1.71 mmol) of 3S-1,2,3,4-tetrahydro-β-carboline-3-carboxylic acid in 4 ml of anhydrous alcohol. The mixed solution was stirred at room temperature for 40 min and evaporated to give a white powder. The obtained white powder was dissolved in 5 ml of anhydrous N,N-dimethylformamide and to this solution 0.2 ml (1.75 mmol) of benzyl bromide were added. The reaction mixture was stirred at 50° C. for 16 h. The resulted precipitates of CsBr were removed by filtration and the filtrate was evaporated to dryness. The residue was dissolved in 30 ml of ethyl acetate and washed successively with saturated $Na_2CO_3$ aqueous (30 ml×3), saturated NaCl aqueous (30 ml×3) and $KHSO_4$ aqueous (5%, 30 ml×3). The separated ethyl acetate layer was dried with anhydrous $MgSO_4$, and then evaporated to provide 0.21 g (78%) of the title compound as a colorless powder. mp. 180–182° C.; EI/MS: 307 [M+H]$^+$; $^1$H NMR (BHSC-500, DMSO-$d_6$): δ=8.79(s, 1H) 7.48(d, J=7.5 Hz, 1H), 7.40(d, J=7.2 Hz, 2H), 7.33(t, J=8.0 Hz, 1H), 7.20(t, J=7.6 Hz, 2H), 7.08(t, J=8.0 Hz, 1H), 7.01(t, J=7.5 Hz, 1H), 6.99(t, J=7.5 Hz, 1H), 4.22(d, J=4.8 Hz, 1H), 3.69(dd, J=10.5 Hz, J=5.0 Hz, 1H), 3.56 (s, 2H), 3.14(dd, J=10.5 Hz, J=2.4 Hz, 1H), 2.83 (ddd, J=10.5 Hz, J=5.0 Hz, J=2.4 Hz, 1H), 2.81(s, 1H).

EXAMPLE 4

The preparation of Boc-Lys (ClZ)-OBzl

The solution of 160 mg (0.491 mmol) of $Cs_2CO_3$ in 0.1 ml of distilled water was added to the solution of 400 mg (0.966 mmol) of Boc-Lys(ClZ)-OH in 2 ml of anhydrous ethanol. The mixture was stirred at room temperature for 40 min and then evaporated to dry. The residue was dried over anhydrous $CaCl_2$ to provide a colorless powder which was dissolved in 1 ml of DMF. To the DMF solution 0.112 ml (0.98 mmol) of benzyl bromide was added slowly. The mixture was stirred at 50° C. for 16 hr and the formed precipitates of CsBr were filteled. The filtrate was evaporated to dry. The residue was dissolved in 20 ml of ethyl acetate and the solution was washed with saturated solution of $NaHCO_3$, NaCl and 5% solution of $KHSO_4$ successively. The organic phase was separated and dried over anhydrous $NaSO_4$. After filtration the filtrate was evaporated at 37° C. to provide 480 mg (98.5%) of the title compound as a colorless syrupy.

EXAMPLE 5

The preparation of HCl. Lys(ClZ)-OBzl

The solution of 100 mg (0.2 mmol) of Boc-Lys(ClZ)-OBzl in 3 ml of hydrogen chloride in ethyl acetate (4 mol/L) was stirred at room temperature for 2 h and TLC (chloroform/methanol, 40:1) indicated complete disappearance of Boc-Lys(ClZ)-OBzl. The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 6

The preparation of Boc-Ala-Lys(ClZ)-OBzl

At 0° C. the solution of 88 mg (0.2 mmol) of HCl.Lys (ClZ)-OBzl in 5 ml of anhydrous tetrahydrofuran was adjusted to pH 9, to which the pre-cold solution of 38 mg (0.2 mmol) of Boc-Ala-OH, 30 mg (0.22 mmol) of 1-hydroxybenzotriazole and 45 mg (0.22 mmol) of dicyclohexylcarbodiimide in 5 ml of anhydrous tetrahydrofuran was added. The reaction mixture was stirred at 0° C. for 2 h and at room temperature for 5 h and TLC (chloroform/methanol, 30:1) indicated complete disappearance of Boc-Ala-OH. The resulted precipitates of N,N-dicyclohexylurea were filtrated and the filtrate was diluted with 20 ml of ethyl acetate. The solution obtained was washed successively with saturated $NaCO_3$ in water (30 ml×3), saturated NaCl in water (30 ml×3) and $KHSO_4$ in water (5%, 30 ml×3). The separated ethyl acetate layer was dried with anhydrous $MgSO_4$, and then evaporated to provide 112 mg (98%) of the title compound as a colorless powder. Mp94–96° C., FAB-MS (m/e) 575[M+H]$^+$, 475[M-Boc]$^+$.

EXAMPLE 7

The preparation of HCl.Ala-Lys(ClZ)-OBzl

The solution of 115 mg (0.2 mmol) of Boc-Ala-Lys(ClZ)-OBzl in 4 ml of hydrogen chloride in ethyl acetate (4 mol/L) was stirred at room temperature for 2 h and TLC (chloroform/methanol, 30:1) indicated complete disappearance of Boc-Ala-Lys(ClZ)-OBzl. The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 8

The preparation of Boc-Pro-Ala-Lys(ClZ)-OBzl

At 0° C. the solution of 657 mg (1.28 mmol) of HCl.Ala-Lys(ClZ)-OBzl in 5 ml of anhydrous tetrahydrofuran was adjusted to pH 9, to which the pre-cold solution of 280 mg (1.3 mmol) of Boc-Pro-OH, 170 mg (1.26 mmol) of 1-hydroxybenzotriazole and 270 mg (1.31 mmol) of dicyclohexylcarbodiimide in 30 ml of anhydrous tetrahydrofuran was added. The reaction mixture was stirred at 0° C. for 2 h and at room temperature for 6 h and TLC (chloroform/methanol, 20:1) indicated complete disappearance of HCl.Ala-Lys(ClZ)-OBzl. The resulted precipitates of N,N-dicyclohexylurea were filtrated and the filtrate was diluted with 80 ml of ethyl acetate. The solution obtained was washed successively with saturated $NaCO_3$ in water (50 ml×3), saturated NaCl in water (50 ml×3) and $KHSO_4$ in water (5%, 30 ml×3). The separated ethyl acetate layer was dried with anhydrous $MgSO_4$, and then evaporated to provide 134 mg (98%) of the title compound as a colorless powder. Mp86–88° C., FAB-MS (m/e) 674[M+H]$^+$.

EXAMPLE 9

The preparation of HCl.Pro-Ala-Lys(ClZ)-OBzl

The solution of 128 mg (0.19 mmol) of Boc-Pro-Ala-Lys(ClZ)-OBzl in 5 ml of hydrogen chloride in ethyl acetate (4 mol/L) was stirred at room temperature for 2 h and TLC (chloroform/methanol, 20:1) indicated complete disappearance of Boc-Pro-Ala-Lys(ClZ)-OBzl. The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 10

The preparation of Boc-Arg(Tos)-Pro-Ala-Lys(ClZ)-OBzl (SEQ ID NO: 12)

At 0° C. the solution of 45 mg (0.074 mmol) of HCl Pro-Ala-Lys(ClZ)-OBzl in 5 ml of anhydrous tetrahydrofuran was adjusted to pH 9, to which the pre-cold solution of 33 mg (0.077 mmol) of Boc-Arg(Tos)-OH, 10 mg (0.074 mmol) of 1-hydroxybenzotriazole and 16 mg (0.077 mmol) of dicyclohexylcarbodiimide in 30 ml of anhydrous tetrahydrofuran was added. The reaction mixture was stirred at 0° C. for 2 h and at room temperature for 6 h and TLC (chloroform/methanol, 15:1) indicated complete disappearance of HCl Pro-Ala-Lys(ClZ)-OBzl. The resulted precipitates of N,N-dicyclohexylurea were filtrated and the filtrate was diluted with 20 ml of ethyl acetate. The solution obtained was washed successively with saturated $NaCO_3$ in water (20 ml×3), saturated NaCl in water (20 ml×3) and $KHSO_4$ in water (5%, 20 ml×3). The separated ethyl acetate layer was dried with anhydrous $MgSO_4$, and then evaporated to provide 70 mg (96%) of the title compound as a colorless powder. Mp68–70° C., FAB-MS (m/e) 984[M+H]$^+$.

EXAMPLE 11

The preparation of HCl.Arg(Tos)-Pro-Ala-Lys(ClZ)-OBzl (SEQ ID NO: 12)

The solution of 128 mg (0.13 mmol) Boc-Arg(Tos)-Pro-Ala-Lys(ClZ)-OBzl (SEQ ID NO: 12) in 5 ml of hydrogen chloride in ethyl acetate (4 mol/L) was stirred at room temperature for 5 h and TLC (chloroform/methanol, 15:1) indicated complete disappearance of Boc-Arg(Tos)-Pro-Ala-Lys(ClZ)-OBzl (SEQ ID NO: 12). The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 12

The preparation of Boc-Ala-Arg(Tos)-Pro-Ala-Lys(ClZ)-OBzl (SEQ ID NO: 13)

At 0° C. the solution of 1490 mg (1.63 mmol) of HCl.Arg(Tos)-Pro-Ala-Lys(ClZ)-OBzl (SEQ ID NO: 12) in 25 ml of anhydrous tetrahydrofuran was adjusted to pH 9, to which the pre-cold solution of 320 mg (169 mmol) of Boc-Ala-OH, 220 mg (1.63 mmol) of 1-hydroxybenzotriazole and 350 mg (1.70 mmol) of dicyclohexylcarbodiimide in 40 ml of anhydrous tetrahydrofuran was added. The reaction mixture was stirred at 0° C. for 2 h and at room temperature for 16 h and TLC (chloroform/methanol, 10:1) indicated complete disappearance of HCl.Arg(Tos)-Pro-Ala-Lys(ClZ)-OBzl (SEQ ID NO: 12). The resulted precipitates of N,N-dicyclohexylurea were filtrated and the filtrate was diluted with 100 ml of ethyl acetate. The solution obtained was washed successively with saturated $NaCO_3$ in water (50 ml×3), saturated NaCl in water (50 ml×3) and $KHSO_4$ in water (5%, 50 ml×3). The separated ethyl acetate layer was dried with anhydrous $MgSO_4$, and then evaporated. The residue was purified on sinica gel chromatography ($CHCl_3/CH_3OH$, 30/1) to provide 1620 mg (94%) of the title compound as a glassy mass. Mp 96–98° C., FAB-MS (m/e) 1076.7[M+Na]$^+$, 1093.4[M+K]$^+$, 954.9[M-Boc]$^+$.

EXAMPLE 13

The preparation of Boc-Gly-Arg(Tos)-Pro-Ala-Lys(ClZ)-OBzl (SEQ ID NO: 14)

At 0° C. the solution of 930 mg (1.01 mmol) of HCl.Arg(Tos)-Pro-Ala-Lys(ClZ)-OBzl (SEQ ID NO: 12) in 15 ml of anhydrous tetrahydrofuran was adjusted to pH 9, to which the pre-cold solution of 200 mg (1.14 mmol) of Boc-Gly-OH, 150 mg (1.11 mmol) of 1-hydroxybenzotriazole and 235 mg (1.14 mmol) of dicyclohexylcarbodiimide in 40 ml of anhydrous tetrahydrofuran was added. The reaction mixture was stirred at 0° C. for 2 h and at room temperature for 12 h and TLC (chloroform/methanol, 10:1) indicated complete disappearance of HCl.Arg(Tos)-Pro-Ala-Lys(ClZ)-OBzl (SEQ ID NO: 12). The resulted precipitates of N,N-dicyclohexylurea were filtrated and the filtrate was diluted with 100 ml of ethyl acetate. The solution obtained was washed successively with saturated $NaCO_3$ in water (50 ml×3), saturated NaCl in water (50 ml×3) and $KHSO_4$ in water (5%, 50 ml×3). The separated ethyl acetate layer was dried with anhydrous $MgSO_4$, and then evaporated. The residue was purified on sinica gel chromatography ($CHCl_3/CH_3OH$, 30/1) to provide 770 mg (73%) of the title compound as a glassy mass. Mp 82–84° C., FAB-MS (m/e) 1038.6[M+H]$^+$, 1061.7[M+Na]$^+$.

EXAMPLE 14

The preparation of Boc-Lys(ClZ)-Arg(Tos)-Pro-Ala-Lys(ClZ)-OBzl (SEQ ID NO: 15)

At 0° C. the solution of 746 mg (0.81 mmol) of HCl.Arg(Tos)-Pro-Ala-Lys(ClZ)-OBzl (SEQ ID NO: 12) in 50 ml of anhydrous tetrahydrofuran was adjusted to pH 9, to which the pre-cold solution of 340 mg (0.82 mmol) of Boc-Lys(ClZ)-OH, 110 mg (0.82 mmol) of 1-hydroxybenzotriazole and 170 mg (0.82 mmol) of dicyclohexylcarbodiimide in 40 ml of anhydrous tetrahydrofuran was added. The reaction mixture was stirred at 0° C. for 2 h and at room temperature for 16 h and TLC (chloroform/methanol, 10:1) indicated complete disappearance of HCl.Arg(Tos)-Pro-Ala-Lys(ClZ)-OBzl (SEQ ID NO: 12). The resulted precipitates of N,N-dicyclohexylurea were filtrated and the filtrate was diluted with 100 ml of ethyl acetate. The solution obtained was washed successively with saturated $NaCO_3$ in water (50 ml×3), saturated NaCl in water (50 ml×3) and $KHSO_4$ in water (5%, 50 ml×3). The separated ethyl acetate layer was dried with anhydrous $MgSO_4$, and then evaporated. The residue was purified on sinica gel chromatography (CHCl$_3$/CH$_3$OH, 30/1) to provide 850 mg (81%) of the title compound as a glassy mass. Mp 78–88° C., FAB-MS (m/e) 1111.3[M+H]$^+$, 1132.5[M+Na]$^+$, 1010.0[M-Boc]$^+$.

EXAMPLE 15

The preparation of Boc-Gln-Arg(Tos)-Pro-Ala-Lys (ClZ)-OBzl (SEQ ID NO: 16)

At 0° C. the solution of 467 mg (0.51 mmol) of HCl.Arg (Tos)-Pro-Ala-Lys(ClZ)-OBzl (SEQ ID NO: 12) in 20 ml of anhydrous tetrahydrofuran was adjusted to pH 9, to which he pre-cold solution of 195 mg, (0.53 mmol) of Boc-Gln-Onp in 10 ml of anhydrous tetrahydrofuran was added. The reaction mixture was stirred at room temperature for 96 h and TLC (chloroform/methanol, 9:1) indicated complete disappearance of HCl.Arg(Tos)-Pro-Ala-Lys(ClZ)-OBzl (SEQ ID NO: 12). The reaction mixture was evaporated to dryness and the residue was purified on sinica gel chromatography (CHCl$_3$/CH$_3$OH, 10:1) to provide 450 mg (80%) of the title compound as a glassy mass. Mp 80–82° C., FAB-MS (m/e) 1111.3[M+H]$^+$, 1132.5[M+Na]$^+$,1010.0[M-Boc]$^+$.

EXAMPLE 16

The preparation of Boc-Asn-Arg(Tos)-Pro-Ala-Lys (ClZ)-OBzl (SEQ ID NO: 17)

At 0° C. the solution of 1160 mg (1.26 mmol) of HCl.Arg (Tos)-Pro-Ala-Lys(ClZ)-OBzl (SEQ ID NO: 12) in 50 ml of anhydrous tetrahydrofuran was adjusted to pH 9, to which the pre-cold solution of 500 mg (1.41 mmol) of Boc-Asn-ONp in 10 ml of anhydrous tetrahydrofuran was added. The reaction mixture was stirred at room temperature for 96 h and TLC (chloroform/methanol, 9:1) indicated complete disappearance of HCl.Arg(Tos)-Pro-Ala-Lys(ClZ)-OBzl (SEQ ID NO: 12). The reaction mixture was evaporated to dryness and the residue was purified on sinica gel chromatography (CHCl$_3$/CH$_3$OH, 10:1) to provide 800 mg (57%) of the title compound as a glassy mass. Mp 86–88° C., FAB-MS (m/e) 1097[M+H]$^+$.

EXAMPLE 17

The preparation of Boc-Arg(Tos)-Arg(Tos)-Pro-Ala-Lys-(ClZ)-OBzl (SEQ ID NO: 18)

At 0° C. the solution of 1636 mg (1.78 mmol) of HCl.Arg (Tos)-Pro-Ala-Lys(ClZ)-OBzl (SEQ ID NO: 12) in 50 ml of anhydrous tetrahydrofuran was adjusted to pH 9, to which the pre-cold solution of 760 mg (1.77 mmol) Boc-Arg(Tos)-OH, 240 mg (1.78 mmol) of 1-hydroxybenzotriazole and 370 mg (1.80 mmol) of dicyclohexylcarbodiimide in 40 ml of anhydrous tetrahydrofuran was added. The reaction mixture was stirred at 0° C. for 2 h and at room temperature for 16 h and TLC (chloroform/methanol, 10:1) indicated complete disappearance of HCl.Arg(Tos)-Pro-Ala-Lys(ClZ)-OBzl (SEQ ID NO: 12). The resulted precipitates of N,N-dicyclohexylurea were filtrated and the filtrate was diluted with 100 ml of ethyl acetate. The solution obtained was washed successively with saturated NaCO$_3$ in water (50 ml×3), saturated NaCl in water (50 ml×3) and KHSO$_4$ in water (5%, 50 ml×3). The separated ethyl acetate layer was dried with anhydrous MgSO$_4$, and then evaporated. The residue was purified on sinica gel chromatography (CHCl$_3$/CH$_3$OH, 30/1) to provide 1330 mg (58%) of the title compound as a glassy mass. Mp 90–92° C., FAB-MS (m/e) 1293[M+H]$^+$.

EXAMPLE 18

The preparation of H-Ala-Arg-Pro-Ala-Lys-OH (1) (SEQ ID NO: 1)

The solution of 250 mg (0.237 mmol) of Boc-Ala-Arg (Tos)-Pro-Ala-Lys(ClZ)OBzl (SEQ ID NO: 13), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide 100 mg (77.8%) of the title compound. Mp. 224–6° C., FAB-MS (m/e) 542[M+H]$^+$.

EXAMPLE 19

The preparation of H-Gly-Arg-Pro-Ala-Lys-OH (2) (SEQ ID NO: 19)

The solution of 300 mg (0.289 mmol) of Boc-Gly-Arg (Tos)-Pro-Ala-Lys(ClZ)OBzl (SEQ ID NO: 14), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide 109 mg (80%) of the title compound. Mp. 168–170° C., FAB-MS (m/e) 528[M+H]$^+$.

EXAMPLE 20

The preparation of H-Lys-Arg-Pro-Ala-Lys-OH (3) (SEQ ID NO: 5)

The solution of 290 mg (0.227 mmol) of Boc-Lys(ClZ)-Arg(Tos)-Pro-Ala-Lys(ClZ)-OBzl (SEQ ID NO: 15), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide 130 mg (96%) of the title compound. Mp. 168–170° C., FAB-MS (m/e) 599[M+H]$^+$.

EXAMPLE 21

The preparation of H-Gln-Arg-Pro-Ala-Lys-OH (4) (SEQ ID NO: 4)

The solution of 250 mg (0.225 mmol) of Boc-Gln-Arg (Tos)-Pro-Ala-Lys(ClZ)-OBzl (SEQ ID NO: 16), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide 150 mg (98%) of the title compound. Mp. 180–182° C., FAB-MS (m/e) 600[M+H]$^+$.

EXAMPLE 22

The preparation of H-Asn-Arg-Pro-Ala-Lys-OH (5) (SEQ ID NO: 6)

The solution of 102 mg (0.1 mmol) of Boc-Asn-Arg(Tos)-Pro-Ala-Lys(ClZ)-OBzl (SEQ ID NO: 17), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide 43 mg (80%) of the title compound. Mp. 168–170° C., FAB-MS (m/e) 585[M+H]$^+$.

EXAMPLE 23

The preparation of H-Arg-Arg-Pro-Ala-Lys-OH (6) (SEQ ID NO: 20)

The solution of 280 mg (0.188 mmol) of Boc-Arg(Tos)-Arg(Tos)-Pro-Ala-Lys(ClZ)-OBzl (SEQ ID NO: 18), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide 100 mg (85%) of the title compound. Mp. 168–170° C., FAB-MS (m/e) 627[M+H]$^+$.

EXAMPLE 24

The preparation of H-Arg-Pro-Ala-Lys-OH (7) (SEQ ID NO: 3)

The solution of 280 mg (0.285 mmol) of Boc-Arg(Tos)-Pro-Ala-Lys(ClZ)OBzl (SEQ ID NO: 12), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide 110 mg (84%) of the title compound. Mp. 158–160° C., FAB-MS (m/e) 472[M+H]$^+$.

EXAMPLE 25

The preparation of H-Pro-Ala-Lys-OH (8)

The solution of 280 mg (0.417 mmol) of Boc-Pro-Ala-Lys(ClZ)-OBzl, 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide 100 mg (75%) of the title compound. Mp. 150–152° C., FAB-MS (m/e) 315[M+H]$^+$.

EXAMPLE 26

The preparation of Boc-Ala-Arg(Tos)-Pro-Ala-Lys(ClZ)-OH (SEQ ID NO: 13)

At 0° C. to the solution of 100 mg (0.95 mmol) of Boc-Ala-Arg(Tos)-Pro-Ala-Lys(ClZ)-OBzl (SEQ ID NO: 13) in 20 ml of methanol 5 ml of the solution of NaOH in methanol (2 mol/L) were added. The reaction mixture was stirred at 0° C. for 2 h and TLC (chloroform/methanol, 15:1) indicated complete disappearance of Boc-Ala-Arg(Tos)-Pro-Ala-Lys(ClZ)-Obzl (SEQ ID NO: 13). The reaction mixture was neutralized to pH 7 and evaporated at room temperature to remove methanol. The residue was acidified to pH 1–2 with hydrochloric acid (2 mol/L) to provide 880 mg (91%) of the title compound as a colorless powder.

EXAMPLE 27

The preparation of Boc-Gly-Arg(Tos)-Pro-Ala-Lys(ClZ)-OH (SEQ ID NO: 14)

At 0° C. to the solution of 230 mg (0.221 mmol) of Boc-Gly-Arg(Tos)-Pro-Ala-Lys(ClZ)-OBzl (SEQ ID NO: 14) in 6 ml of methanol 5 ml of the solution of NaOH in methanol (2 mol/L) were added. The reaction mixture was stirred at 0° C. for 2 h and TLC (chloroform/methanol, 15:1) indicated complete disappearance of Boc-Gly-Arg(Tos)-Pro-Ala-Lys(ClZ)-OBzl (SEQ ID NO: 14). The reaction mixture was neutralized to pH 7 and evaporated at room temperature to remove methanol. The residue was acidified to pH 1–2 with hydrochloric acid (2 mol/L) to provide 180 mg (86%) of the title compound as a colorless powder.

EXAMPLE 28

The preparation of Boc-Lys(ClZ)-Arg(Tos)-Pro-Ala-Lys(ClZ)-OH (SEQ ID NO: 15)

At 0° C. to the solution of 250 mg (0196 mmol) of Boc-Lys(ClZ)-Arg(Tos)-Pro-Ala-Lys(ClZ)-OBzl (SEQ ID NO: 15) in 6 ml of methanol 5 ml of the solution of NaOH in methanol (2 mol/L) were added. The reaction mixture was stirred at 0° C. for 2 h and TLC (chloroform/methanol, 15:1) indicated complete disappearance of Boc-Lys(ClZ)-Arg(Tos)-Pro-Ala-Lys(ClZ)-Obzl (SEQ ID NO: 15). The reaction mixture was neutralized to pH 7 and evaporated at room temperature to remove methanol. The residue was acidified to pH 1–2 with hydrochloric acid (2 mol/L) to provide 200 mg (86%) of the title compound as a colorless powder.

EXAMPLE 29

The preparation of Boc-Gln-Arg(Tos)-Pro-Ala-Lys(ClZ)-OH (SEQ ID NO: 16)

At 0° C. to the solution of 770 mg (0.694 mmol) of Boc-Gln-Arg(Tos)-Pro-Ala-Lys(ClZ)-OBzl (SEQ ID NO: 16) in 18 ml of methanol 5 ml of the solution of NaOH in methanol (2 mol/L) were added. The reaction mixture was stirred at 0° C. for 2 h and TLC (chloroform/methanol, 15:1) indicated complete disappearance of Boc-Gln-Arg(Tos)-Pro-Ala-Lys(ClZ)-OBzl (SEQ ID NO: 16). The reaction mixture was neutralized to pH 7 and evaporated at room temperature to remove methanol. The residue was acidified to pH 1–2 with hydrochloric acid (2 mol/L) to provide 610 mg (86%) of the title compound as a colorless powder.

EXAMPLE 30

The preparation of Boc-Asn-Arg(Tos)-Pro-Ala-Lys(ClZ)-OH (SEQ ID NO: 17)

At 0° C. to the solution of 300 mg (0.210 mmol) of Boc-Asn-Arg(Tos)-Pro-Ala-Lys(ClZ)-OBzl (SEQ ID NO: 17) in 8 ml of methanol 5 ml of the solution of NaOH in methanol (2 mol/L) were added. The reaction mixture was stirred at 0° C. for 2 h and TLC (chloroform/methanol, 15:1) indicated complete disappearance of Boc-Asn-Arg(Tos)-Pro-Ala-Lys(ClZ)-OBzl (SEQ ID NO: 17). The reaction mixture was neutralized to pH 7 and evaporated at room temperature to remove methanol. The residue was acidified to pH 1–2 with hydrochloric acid (2 mol/L) to provide 230 mg (83%) of the title compound as a colorless powder.

EXAMPLE 31

The preparation of Boc-Arg(Tos)-Arg(Tos)-Pro-Ala-Lys(ClZ)-OH (SEQ ID NO: 18)

At 0° C. to the solution of 600 mg (0.464 mmol) of Boc-Arg(Tos)-Arg(Tos)-Pro-Ala-Lys(ClZ)-OBzl (SEQ ID NO: 18) in 10 ml of methanol 5 ml of the solution of NaOH in methanol (2 mol/L) were added. The reaction mixture was stirred at 0° C. for 2 h and TLC (chloroform/methanol, 15:1) indicated complete disappearance of Boc-Arg(Tos)-Arg(Tos)-Pro-Ala-Lys(ClZ)-OBzl (SEQ ID NO: 18). The reaction mixture was neutralized to pH 7 and evaporated at room temperature to remove methanol. The residue was acidified to pH 1–2 with hydrochloric acid (2 mol/L) to provide 420 mg (76%) of the title compound as a colorless powder.

EXAMPLE 32

The preparation of Boc-Arg(Tos)-Pro-Ala-Lys(ClZ)-OH (SEQ ID NO: 12)

At 0° C. to the solution of 500 mg (0.51 mmol) of Boc-Arg(Tos)-Pro-Ala-Lys(ClZ)-OBzl (SEQ ID NO: 12) in 5 ml of methanol 5 ml of the solution of NaOH in methanol (2 mol/L) were added. The reaction mixture was stirred at 0° C. for 2 h and TLC (chloroform/methanol, 15:1) indicated complete disappearance of Boc-Arg(Tos)-Pro-Ala-Lys(ClZ)-OBzl (SEQ ID NO: 12). The reaction mixture was neutralized to pH 7 and evaporated at room temperature to remove methanol. The residue was acidified to pH 1–2 with hydrochloric acid (2 mol/L) to provide 380 mg (84%) of the title compound as a colorless powder. Mp 108–110° C., TOF-MS (m/e) 893.2[M+H]$^+$, 915.5[M+Na]$^+$, 937.2[M+2Na]$^+$

EXAMPLE 33

The preparation of Boc-Pro-Ala-Lys(ClZ)-OH

At 0° C. to the solution of 135 mg (0.2 mmol) of Boc-Pro-Ala-Lys(ClZ)-OBzl in 5 ml of methanol 5 ml of the solution of NaOH in methanol (2 mol/L) were added. The reaction mixture was stirred at 0° C. for 2 h and TLC (chloroform/methanol, 15:1) indicated complete disappearance of Boc-Pro-Ala-Lys(ClZ)-OBzl. The reaction mixture was neutralized to pH 7 and evaporated at room temperature to remove methanol. The residue was acidified to pH 1–2 with hydrochloric acid (2 mol/L) to provide 100 mg (86%) of the title compound as a colorless powder.

EXAMPLE 34

The preparation of Boc-Pro-OH (1) With Boc-N$_3$ as the acylation agent

At 0° C. the solution of 800 mg (6.96 mmol) of Pro-OH were suspended in 12 ml of anhydrous DMF, to which 1.8 ml of triethylamine were added. The reaction mixture was stirred at 0° C. and then 1.5 ml of Boc-N$_3$ were added during 30 min. After the solids in the reaction mixture were dissolved and a clear solution was obtained. The solution was stirred at room temperature for 3 days and TLC (chloroform/methanol, 30:1) indicated complete disappearance of Pro-OH. The reaction mixture was evaporated to dryness and the residue was dissolved in 50 ml of ethyl acetate. The solution obtained was washed successively with saturated NaCO$_3$ in water (50 ml×3), saturated NaCl in water (50 ml×3) and KHSO$_4$ in water (5%, 50 ml×3). The separated ethyl acetate layer was dried with anhydrous MgSO$_4$, and then evaporated to provide 1200 mg (80%) of the title compound as a crystal.

(2) With (Boc)$_2$O as the acylation agent

At room temperature the solution of 800 mg (6.96 mmol) of Pro-OH were suspended in 12 ml of anhydrous DMF, to which 2.5 ml of triethylamine were added. The reaction mixture was stirred room temperature and then 1625 mg (7.45 mmol) of (Boc)$_2$O were added. After the solids in the reaction mixture were dissolved and a clear solution was obtained. The solution was stirred at room temperature for 24 h and TLC (chloroform/methanol, 30:1) indicated complete disappearance of Pro-OH. The reaction mixture was evaporated to dryness and the residue was dissolved in 50 ml of ethyl acetate. The solution obtained was washed successively with saturated NaCO$_3$ in water (50 ml×3), saturated NaCl in water (50 ml×3) and KHSO$_4$ in water (5%, 50 ml×3). The separated ethyl acetate layer was dried with anhydrous MgSO$_4$, and then evaporated to provide 1350 mg (90%) of the title compound as a crystal.

EXAMPLE 35

The preparation of Boc-Pro-OBzl

The solution of 33 mg (0.10 mmol) of Cs$_2$CO$_3$ in 0.1 ml of distilled water was added to the solution of 43 mg (0.20 mmol) Boc-Pro-OH in 2 ml of anhydrous ethanol. The mixture was stirred at room temperature for 40 min and then evaporated to dryness. The residue was dried over anhydrous $CaCl_2$ to provide a colorless powder which was dissolved in 1 ml of DMF. To the DMF solution 34 mg (0.2 mmol) of benzyl bromide was added slowly. The mixture was stirred at 50° C. for 16 hr and the formed precipitates of CsBr were filteled. The filtrate was evaporated to dry. The residue was dissolved in 20 ml of ethyl acetate and the solution was washed with saturated solution of $NaHCO_3$, NaCl and 5% solution of $KHSO_4$ successively. The organic phase was separated and dried over anhydrous $NaSO_4$. After filtration the filtrate was evaporated at 37° C. to provide 54 mg (88%) of the title compound as a colorless syrupy.

EXAMPLE 36

The preparation of HCl-Pro-OBzl

The solution of 61 mg (0.2 mmol) of Boc-Pro-OBzl in 3 ml of hydrogen chloride in ethyl acetate (4 mol/L) was stirred at room temperature for 2 h and TLC (chloroform/methanol, 30:1) indicated complete disappearance of Boc-Pro-OBzl. The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 37

The preparation of Boc-Arg(Tos)-Pro-OBzl

At 0° C. the solution of 18 mg (0.075 mmol) of HCl Pro-OBzl in 5 ml of anhydrous tetrahydrofuran was adjusted to pH 9, to which the pre-cold solution of 33 mg (0.077 mmol) Boc-Arg(Tos)-OH, 10 mg (0.074 mmol) of 1-hydroxybenzotriazole and 16 mg (0.077 mmol) of dicyclohexylcarbodiimide in 10 ml of anhydrous tetrahydrofuran was added. The reaction mixture was stirred at 0° C. for 2 h and at room temperature for 5 h and TLC (chloroform/methanol, 30:1) indicated complete disappearance of HCl.Arg(Tos)-Pro-Ala-Lys(ClZ)-OBzl (SEQ ID NO: 12). The resulted precipitates of N,N-dicyclohexylurea were filtrated and the filtrate was diluted with 30 ml of ethyl acetate. The solution obtained was washed successively with saturated $NaCO_3$ in water (10 ml×3), saturated NaCl in water (10 ml×3) and $KHSO_4$ in water (5%, 10 ml×3). The separated ethyl acetate layer was dried with anhydrous $MgSO_4$, filtered. The filtrate was evaporated to provide 37 mg (80%) of the title compound as a colorless powder. Mp 60–62° C., FAB-MS (m/e) 617[M+H]$^+$.

EXAMPLE 38

The preparation of HCl.Arg(Tos)-Pro-OBzl

The solution of 123 mg (0.2 mmol) of Boc-Arg(Tos)-Pro-OBzl in 3 ml of hydrogen chloride in ethyl acetate (4 mol/L) was stirred at room temperature for 2 h and TLC (chloroform/methanol, 20:1) indicated complete disappearance of Boc-Arg(Tos)-Pro-OBzl. The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 39

The preparation of Boc-Ala-Arg(Tos)-Pro-OBzl

At 0° C. the solution of 793 mg (1.44 mmol) of HCl.Ala-Lys(ClZ)-OBzl in 5 ml of anhydrous tetrahydrofuran was adjusted to pH 9, to which the pre-cold solution of 280 mg (1.3 mmol) Boc-Ala-OH, 170 mg (1.26 mmol) of 1-hydroxybenzotriazole and 270 mg (1.31 mmol) of dicyclohexylcarbodiimide in 10 ml of anhydrous tetrahydrofuran was added. The reaction mixture was stirred at 0° C. for 2 h and at room temperature for 5 h and TLC (chloroform/methanol, 20:1) indicated complete disappearance of HCl.Ala-Lys(ClZ)-OBzl. The resulted precipitates of N,N-dicyclohexylurea were filtrated and the filtrate was diluted with 30 ml of ethyl acetate. The solution obtained was washed successively with saturated $NaCO_3$ in water (10 ml×3), saturated NaCl in water (10 ml×3) and $KHSO_4$ in water (5%, 10 ml×3). The separated ethyl acetate layer was dried with anhydrous $MgSO_4$, filtered. The filtrate was evaporated to provide the crud product as a powder which was purified on sinica gel chromatography (chloroform/methanol, 30:1) to give 550 mg (55%) of the title compound, as a colorless powder. Mp 86–88° C., FAB-MS (m/e) 685[M+H]$^+$, 724 [M+K]$^+$.

EXAMPLE 40

The preparation of HCl-Ala-Arg(Tos)-Pro-OBzl

The solution of 137 mg (0.2 mmol) of Boc-Ala-Arg(Tos)-Pro-OBzl in 3 ml of hydrogen chloride in ethyl acetate (4 mol/L) was stirred at room temperature for 2 h and TLC (chloroform/methanol, 20:1) indicated complete disappearance of Boc-Ala-Arg(Tos)-Pro-OBzl. The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 41

The preparation of Boc-Ala-Arg(Tos)-Pro-OH

At 0° C. to the solution of 550 mg (0.80 mmol) of Boc-Ala-Arg(Tos)-Pro-OBzl in 10 ml of methanol 5 ml of the solution of NaOH in methanol (2 mol/L) were added. The reaction mixture was stirred at 0° C. for 2 h and TLC (chloroform/methanol, 20:1) indicated complete disappearance of Boc-Ala-Arg(Tos)-Pro-OBzl. The reaction mixture was neutralized to pH 7 and evaporated at room temperature to remove methanol. The residue was acidified to pH 1–2 with hydrochloric acid (2 mol/L) to provide 130 mg (27%) of the title compound as a colorless powder.

EXAMPLE 42

The preparation of H-Ala-Arg-Pro-OH (9)

The solution of 105 mg (0.153 mmol) of Boc-Ala-Arg (Tos)-Pro-Obzl, 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide 10 mg (19%) of the title compound. Mp. 150–152° C., FAB-MS (m/e) 344[M+H]$^+$.

EXAMPLE 43

The preparation of HCl.Ala-OBzl

To the solution of 25 ml of benzyl alcohol and 5 g of polyphosphoric acid 1070 mg (0.012 mmol) of L-Ala were added. The reaction mixture was stirred at 90–95□ for 4 h and TLC (chloroform/methanol, 20:1) indicated complete disappearance of L-Ala. The reaction mixture was pured into the solution of 10 ml of concentrated hydrochloric acid in 200 ml of water. The formed solution was extracted with ether (50 ml×3) and separated. The organic phase was washed with hydrochloric acid (2%, 30 ml×3). The combined water phases was adjusted to pH10 with sodium carbonate. The water phase was extracted with 100 ml of etherand then dried over anhydrous $Na_2SO_4$. After filtration to the filtrate hydrogen chloride gas was introduced to precipitate the title compound. The precipitates were filtered and dry over anhydrous $CaCl_2$ to provide 1500 mg (58%) of the title compound as a crystal. Mp140–142° C.

EXAMPLE 44

The preparation of Boc-Pro-Ala-OBzl

At 0° C. the solution of 500 mg (2.326 mmol) of HCl Ala-OBzl in 5 ml of anhydrous tetrahydrofuran was adjusted to pH 9, to which the pre-cold solution of 500 mg (2.326 mmol) of Boc-Pro-OH, 300 mg (2.222 mmol) of 1-hydroxybenzotriazole and 480 mg (2.331 mmol) of dicyclohexylcarbodiimide in 30 ml of anhydrous tetrahydrofuran was added. The reaction mixture was stirred at 0° C. for 2 h and at room temperature for 6 h and TLC (chloroform/methanol, 30:1) indicated complete disappearance of HCl.Ala-Lys(ClZ)-OBzl. The resulted precipitates of N,N-dicyclohexylurea were filtrated and the filtrate was diluted with 80 ml of ethyl acetate. The solution obtained was washed successively with saturated $NaCO_3$ in water (50 ml×3), saturated NaCl in water (50 ml×3) and $KHSO_4$ in water (5%, 30 ml×3). The separated ethyl acetate layer was dried with anhydrous $MgSO_4$, and then evaporated to provide 782 mg (89%) of the title compound as a colorless powder. Mp100–101° C., FAB-MS (m/e) 377[M+H]$^+$.

EXAMPLE 45

The preparation of HCl.Pro-Ala-OBzl

The solution of 75 mg (0.2 mmol) of Boc-Pro-Ala-OBzl in 3 ml of hydrogen chloride in ethyl acetate (4 mol/L) was stirred at room temperature for 2 h and TLC (chloroform/methanol, 30:1) indicated complete disappearance of Boc-Pro-Ala-OBzl. The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 46

The preparation of Boc-Arg(Tos)-Pro-Ala-OBzl

At 0° C. the solution of 72 mg (0.231 mmol) of HCl.Pro-Ala-OBzl in 15 ml of anhydrous tetrahydrofuran was adjusted to pH 9, to which the pre-cold solution of 100 mg (0.234 mmol) of Boc-Arg(Tos)-OH, 31 mg (0.230 mmol) of 1-hydroxybenzotriazole and 48 mg (0.233 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 30:1) indicated complete disappearance of HCl.Pro-Ala-OBzl. The resulted precipitates of N,N-dicyclohexylurea were filtrated and the filtrate was diluted with 80 ml of ethyl acetate. The solution obtained was washed successively with saturated $NaCO_3$ in water (50 ml×3), saturated NaCl in water (50 ml×3) and $KHSO_4$ in water (5%, 30 ml×3). The separated ethyl acetate layer was dried with anhydrous $MgSO_4$, and then evaporated to provide 120 mg (75.6%) of the title compound as a colorless powder. Mp70–71.5° C., FAB-MS (m/e) 688[M+H]$^+$.

EXAMPLE 47

The preparation of HCl.Arg(Tos)-Pro-Ala-OBzl

The solution of 137 mg (0.2 mmol) of Boc-Arg(Tos)-Pro-Ala-OBzl in 3 ml of hydrogen chloride in ethyl acetate (4 mol/L) was stirred at room temperature for 2 h and TLC (chloroform/methanol, 30:1) indicated complete disappearance of Boc-Arg(Tos)-Pro-Ala-OBzl. The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 48

The preparation of Boc-Ala-Arg(Tos)-Pro-Ala-OBzl (SEQ ID NO: 7)

At 0° C. the solution of 45 mg (0.072 mmol) of HCl.Arg(Tos)-Pro-Ala-OBzl in 15 ml of anhydrous tetrahydrofuran was adjusted to pH 9, to which the pre-cold solution of 15 mg (0.079 mmol) Boc-Ala-OH, 10 mg (0.074 mmol) of 1-hydroxybenzotriazole and 16 mg (0.077 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 30:1) indicated complete disappearance of HCl.Arg(Tos)-Pro-Ala-OBzl. The resulted precipitates of N,N-dicyclohexylurea were filtrated and the filtrate was diluted with 80 ml of ethyl acetate. The solution obtained was washed successively with saturated $NaCO_3$ in water (50 ml×3), saturated NaCl in water (50 ml×3) and $KHSO_4$ in water (5%, 30 ml×3). The separated ethyl acetate layer was dried with anhydrous $MgSO_4$, and then evaporated to provide 30 mg (54%) of the title compound as a colorless powder. Mp 80–82° C., FAB-MS (m/e) 758[M+H]$^+$.

EXAMPLE 49

The preparation of HCl.Ala-Arg(Tos)-Pro-Ala-OBzl (SEQ ID NO: 7)

The solution of 151 mg (0.2 mmol) of Boc-Ala-Arg(Tos)-Pro-Ala-OBzl (SEQ ID NO: 7) in 3 ml of hydrogen chloride in ethyl acetate (4 mol/L) was stirred at room temperature for 2 h and TLC (chloroform/methanol, 30:1) indicated complete disappearance of Boc-Ala-Arg(Tos)-Pro-Ala-OBzl (SEQ ID NO: 7). The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 50

The preparation of Boc-Ala-Arg(Tos)-Pro-Ala-OH (SEQ ID NO: 7)

At 0° C. to the solution of 550 mg (0.726 mmol) of Boc-Ala-Arg(Tos)-Pro-Ala-OBzl (SEQ ID NO: 7) in 20 ml of methanol 8 ml of the solution of NaOH in methanol (2 mol/L) were added. The reaction mixture was stirred at 0° C. for 2 h and TLC (chloroform/methanol, 15:1) indicated complete disappearance of Boc-Asn-Arg(Tos)-Pro-Ala-Lys(ClZ)-OBzl (SEQ ID NO: 17). The reaction mixture was neutralized to pH 7 and evaporated at room temperature to remove methanol. The residue was acidified to pH 1–2 with hydrochloric acid (2 mol/L) to provide 330 mg (67%) of the title compound as a colorless powder.

EXAMPLE 51

The preparation of H-Ala-Arg-Pro-Ala-OH (10) (SEQ ID NO: 2)

The solution of 250 mg (0.330 mmol) of Boc-Ala-Arg(Tos)-Pro-Ala-OBzl (SEQ ID NO: 7), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide 80 mg (58%) of the title compound. Mp. 157–159° C., FAB-MS (m/e) 415[M+H]$^+$.

EXAMPLE 52

The preparation of 3S-[2-Boc-Pro-Ala-Lys(ClZ)]-1,2,3,4-tetrahydro-β-carboline-3-carboxylic acid benzyl ester At 0° C. the solution of 320 mg (1.046 mmol) of 3S-1,2,3,4-tetrahydro-β-carboline-3-carboxylic acid benzyl ester in 25 ml of anhydrous tetrahydrofuran was adjusted to pH 9, to which the pre-cold solution of 600 mg (1.031 mmol) of Boc-Pro-Ala-Lys(ClZ)-OH, 140 mg (1.037 mmol) of 1-hydroxybenzotriazole and 220 mg (1.068 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 30:1) indicated complete disappearance of Boc-Pro-Ala-Lys(ClZ)-OH. The resulted precipitates of N,N-dicyclohexylurea were filtrated and the filtrate was diluted with 80 ml of ethyl acetate. The solution obtained was washed successively with saturated NaCO$_3$ in water (50 ml×3), saturated NaCl in water (50 ml×3) and KHSO$_4$ in water (5%, 30 ml×3). The separated ethyl acetate layer was dried with anhydrous MgSO$_4$, and then evaporated to provide 890 mg (98%) of the title compound as a colorless powder. Mp 68–70° C., FAB-MS (m/e) 872[M+H]$^+$.

EXAMPLE 53

The preparation of 3S-(2-Boc)-1,2,3,4-tetrahydro-β-carboline-3-carboxyl-Pro-Ala-Lys(ClZ)-OBzl At 0° C. the solution of 390 mg (0.670 mmol) of HCl Pro-Ala-Lys(ClZ)-OBzl in 15 ml of anhydrous tetrahydrofuran was adjusted to pH 9, to which the pre-cold solution of 210 mg (0.686 mmol) of 3S-(2-Boc)-1,2,3,4-tetrahydro-β-carboline-3-carboxylic acid (100 mg (0.149 mmol) of 1-hydroxybenzotriazole and 150 mg (0.728 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 30:1) indicated complete disappearance of HCl Pro-Ala-Lys(ClZ)-OBzl. The resulted precipitates of N,N-dicyclohexylurea were filtrated and the filtrate was diluted with 80 ml of ethyl acetate. The solution obtained was washed successively with saturated NaCO$_3$ in water (50 ml×3), saturated NaCl in water (50 ml×3) and KHSO$_4$ in water (5%, 30 ml×3). The separated ethyl acetate layer was dried with anhydrous MgSO$_4$, and then evaporated to provide 520 mg (89%) of the title compound as a colorless powder. Mp 76–78° C., FAB-MS (m/e) 870 [M+H]$^+$.

EXAMPLE 54

The preparation of 3S-[2-Boc-Ala-Arg(Tos)-Pro]-1,2,3,4-tetra-hydro-β-carboline-3-carboxylic acid benzyl ester At 0° C. the solution of 320 mg (1.046 mmol) of 3S-1,2,3,4-tetrahydro-β-carboline-3-carboxylic acid benzyl ester in 25 ml of anhydrous tetrahydrofuran was adjusted to pH 9, to which the pre-cold solution of 130 mg (0.218 mmol) of Boc-Ala-Arg(Tos)-Pro-OH, 30 mg (0.222 mmol) of 1-hydroxybenzotriazole and 45 mg (0.218 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 30:1) indicated complete disappearance of Boc-Ala-Arg(Tos)-Pro-OH. The resulted precipitates of N,N-dicyclohexylurea were filtrated and the filtrate was diluted with 80 ml of ethyl acetate. The solution obtained was washed successively with saturated NaCO$_3$ in water (50 ml×3), saturated NaCl in water (50 ml×3) and KHSO$_4$ in water (5%, 30 ml×3). The separated ethyl acetate layer was dried with anhydrous MgSO$_4$, and then evaporated to provide 140 mg (73%) of the title compound as a colorless powder. Mp 70–72° C., FAB-MS (m/e) 886[M+H]$^+$.

EXAMPLE 55

The preparation of 3S-(2-Boc)-1,2,3,4-tetrahydro-β-carboline-3-carboxyl-Ala-Arg(Tos)-Pro-OBzl At 0° C. the solution of 208 mg (0.335 mmol) of HCl Ala-Arg(Tos)-Pro-OBzl in 15 ml of anhydrous tetrahydrofuran was adjusted to pH 9, to which the pre-cold solution of 110 mg (0.348 mmol) of 3S-(2-Boc)-1,2,3,4-tetrahydro-β-carboline-3-carboxylic acid, 45 mg (0.333 mmol) of 1-hydroxybenzotriazole and 72 mg (0.350 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 30:1) indicated complete disappearance of HCl Ala-Arg(Tos)-Pro-OBzl. The resulted precipitates of N,N-dicyclohexylurea were filtrated and the filtrate was diluted with 80 ml of ethyl acetate. The solution obtained was washed successively with saturated $NaCO_3$ in water (50 ml×3), saturated NaCl in water (50 ml×3) and $KHSO_4$ in water (5%, 30 ml×3). The separated ethyl acetate layer was dried with anhydrous $MgSO_4$, and then evaporated to provide 150 mg (51%) of the title compound as a colorless powder. Mp 76–78° C., FAB-MS (m/e) 883$[M+H]^+$.

EXAMPLE 56

The preparation of 3S-[2-Boc-Arg(Tos)-Pro-Ala-Lys(ClZ)]-1,2,3,4-tetrahydro-β-carboline-3-carboxylic acid benzyl ester (SEQ ID NO: 12)

At 0° C. the solution of 100 mg (0.326 mmol) of 3S-1,2,3,4-tetrahydro-β-carboline-3-carboxylic acid benzyl ester in 25 ml of anhydrous tetrahydrofuran was adjusted to pH 9, to which the pre-cold solution of 290 mg (0.338 mmol) of Boc-Arg(Tos)-Pro-Ala-Lys(ClZ)-OH (SEQ ID NO: 12), 40 mg (0.296 mmol) of 1-hydroxybenzotriazole and 70 mg (0.340 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of Boc-Arg(Tos)-Pro-Ala-Lys(ClZ)-OH (SEQ ID NO: 12). The resulted precipitates of N,N-dicyclohexylurea were filtrated and the filtrate was diluted with 80 ml of ethyl acetate. The solution obtained was washed successively with saturated $NaCO_3$ in water (50 ml×3), saturated NaCl in water (50 ml×3) and $KHSO_4$ in water (5%, 30 ml×3). The separated ethyl acetate layer was dried with anhydrous $MgSO_4$, and then evaporated to provide 340 mg (89%) of the title compound as a colorless powder. Mp 114–6° C., FAB-MS (m/e) 884$[M+H]^+$.

EXAMPLE 57

The preparation of 3S-(2-Boc)-1,2,3,4-tetrahydro-β-carboline-3-carboxyl-Arg(Tos)-Pro-Ala-Lys(ClZ)-OBzl (SEQ ID NO: 12)

At 0° C. the solution of 450 mg (0.490 mmol) of HCl Arg(Tos)-Pro-Ala-Lys(ClZ)-OBzl (SEQ ID NO: 12) in 15 ml of anhydrous tetrahydrofuran was adjusted to pH 9, to which the pre-cold solution of 180 mg (0.570 mmol) of 3S-(2-Boc)-1,2,3,4-tetrahydro-β-carboline-3-carboxylic acid, 70 mg (0.58 mmol) of 1-hydroxybenzotriazole and 120 mg (0.582 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of HCl Arg(Tos)-Pro-Ala-Lys-(ClZ)-OBzl (SEQ ID NO: 12). The resulted precipitates of N,N-dicyclohexylurea were filtrated and the filtrate was diluted with 80 ml of ethyl acetate. The solution obtained was washed successively with saturated $NaCO_3$ in water (50 ml×3), saturated NaCl in water (50 ml×3) and $KHSO_4$ in water (5%, 30 ml×3). The separated ethyl acetate layer was dried with anhydrous $MgSO_4$, and then evaporated to provide 500 mg (83%) of the title compound as a colorless powder. Mp 94–96° C., FAB-MS (m/e) 1182 $[M+H]^+$, 1214 $[M+CH_3OH]^+$.

EXAMPLE 58

The preparation of 3S-[2-Boc-Ala-Arg(Tos)-Pro-Ala]-1,2,3,4-tetrahydro-β-carboline-3-carboxylic acid benzyl ester (SEQ ID NO: 7)

At 0° C. the solution of 160 mg (0.522 mmol) of 3S-1,2,3,4-tetrahydro-β-carboline-3-carboxylic acid benzyl ester in 25 ml of anhydrous tetrahydrofuran was adjusted to pH 9, to which the pre-cold solution of 330 mg (0.495 mmol) of Boc-Ala-Arg(Tos)-Pro-Ala-OH (SEQ ID NO: 7), 70 mg (0.518 mmol) of 1-hydroxybenzotriazole and 110 mg (534 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of Boc-Ala-Arg(Tos)-Pro-Ala-OH (SEQ ID NO: 7). The resulted precipitates of N,N-dicyclohexylurea were filtrated and the filtrate was diluted with 80 ml of ethyl acetate. The solution obtained was washed successively with saturated $NaCO_3$ in water (50 ml×3), saturated NaCl in water (50 ml×3) and $KHSO_4$ in water (5%, 30 ml×3). The separated ethyl acetate layer was dried with anhydrous $MgSO_4$, and then evaporated to provide 200 mg (42%) of the title compound as a colorless powder. Mp 104–6° C., FAB-MS (m/e) 1183$[M+H]^+$.

EXAMPLE 59

The preparation of 3S-(2-Boc)-1,2,3,4-tetrahydro-β-carboline-3-carboxyl-Ala-Arg(Tos)-Pro-Ala-OBzl (SEQ ID NO: 7)

At 0° C. the solution of 250 mg (0.361 mmol) of HCl Ala-Arg(Tos)-Pro-Ala-OBzl (SEQ ID NO: 7) in 15 ml of anhydrous tetrahydrofuran was adjusted to pH 9, to which the pre-cold solution of 120 mg (0.392 mmol) of 3S-(2-Boc)-1,2,3,4-tetrahydro-β-carboline-3-carboxylic acid, 50 mg (0.370 mmol) of 1-hydroxybenzotriazole and 80 mg (0.388 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of HCl Ala-Arg(Tos)-Pro-Ala-OBzl (SEQ ID NO: 7). The resulted precipitates of N,N-dicyclohexylurea were filtrated and the filtrate was diluted with 80 ml of ethyl acetate. The solution obtained was washed successively with saturated $NaCO_3$ in water (50 ml×3), saturated NaCl in water (50 ml×3) and $KHSO_4$ in water (5%, 30 ml×3). The separated ethyl acetate layer was dried with anhydrous $MgSO_4$, and then evaporated to provide 160 mg (45%) of the title compound as a colorless powder. Mp 98–100° C., FAB-MS (m/e) 957$[M+H]^+$.

EXAMPLE 60

The preparation of HCl-Ala-Arg(Tos)-Pro-Ala-Lys (ClZ)-OBzl (SEQ ID NO: 13)

The solution of 100 mg (0.080 mmol) of Boc-Ala-Arg(Tos)-Pro-Ala-Lys(ClZ)-OBzl (SEQ ID NO: 13) in 3 ml of hydrogen chloride in ethyl acetate (4 mol/L) was stirred at room temperature for 2 h and TLC (chloroform/methanol, 10:1) indicated complete disappearance of Boc-Ala-Arg (Tos)-Pro-Ala-Lys(ClZ)-OBzl (SEQ ID NO: 13). The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 61

The preparation of Cl-Gly-Arg(Tos)-Pro-Ala-Lys(ClZ)-OBzl (SEQ ID NO: 14)

The solution of 100 mg (0.081 mmol) of Boc-Gly-Arg(Tos)-Pro-Ala-Lys(ClZ)-OBzl (SEQ ID NO: 14) in 3 ml of hydrogen chloride in ethyl acetate (4 mol/L) was stirred at room temperature for 2 h and TLC (chloroform/methanol, 10:1) indicated complete disappearance of Boc-Gly-Arg(Tos)-Pro-Ala-Lys(ClZ)-OBzl (SEQ ID NO: 14). The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 62

The preparation of HCl Lys(ClZ)-Arg(Tos)-Pro-Ala-Lys(ClZ)-OBzl (SEQ ID NO: 15)

The solution of 100 mg (0.068 mmol) of Boc-Lys(ClZ)-Arg(Tos)-Pro-Ala-Lys(ClZ)-OBzl (SEQ ID NO: 15) in 3 ml of hydrogen chloride in ethyl acetate (4 mol/L) was stirred at room temperature for 2 h and TLC (chloroform/methanol, 10:1) indicated complete disappearance of Boc-Lys(ClZ)-Arg(Tos)-Pro-Ala-Lys(ClZ)-OBzl (SEQ ID NO: 15). The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 63

The preparation of HCl.Gln-Arg(Tos)-Pro-Ala-Lys(ClZ)-OBzl (SEQ ID NO: 16)

The solution of 100 mg (0.076 mmol) Boc-Gln-Arg(Tos)-Pro-Ala-Lys(ClZ)-OBzl (SEQ ID NO: 16) in 3 ml of hydrogen chloride in ethyl acetate (4 mol/L) was stirred at room temperature for 2 h and TLC (chloroform/methanol, 10:1) indicated complete disappearance of Boc-Gln-Arg(Tos)-Pro-Ala-Lys(ClZ)-OBzl (SEQ ID NO: 16). The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 64

The preparation of HCl.Asn-Arg(Tos)-Pro-Ala-Lys(ClZ)-OBzl (SEQ ID NO: 17)

The solution of 100 mg (0.076 mmol) of Boc-Asn-Arg(Tos)-Pro-Ala-Lys(ClZ)-OBzl (SEQ ID NO: 17) in 3 ml of hydrogen chloride in ethyl acetate (4 mol/L) was stirred at room temperature for 2 h and TLC (chloroform/methanol, 10:1) indicated complete disappearance of Boc-Asn-Arg(Tos)-Pro-Ala-Lys(ClZ)-OBzl (SEQ ID NO: 17). The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 65

The preparation of HCl.Arg(Tos)-Arg(Tos)-Pro-Ala-Lys(ClZ)-OBzl (SEQ ID NO: 18)

The solution of 100 mg (0.076 mmol) of Boc-Arg(Tos)-Arg(Tos)-Pro-Ala-Lys(ClZ)-OBzlin (SEQ ID NO: 18) 3 ml of hydrogen chloride in ethyl acetate (4 mol/L) was stirred at room temperature for 2 h and TLC (chloroform/methanol, 10:1) indicated complete disappearance of Boc-Arg(Tos)-Arg(Tos)-Pro-Ala-Lys(ClZ)-OBzl (SEQ ID NO: 18). The reaction mixture was evaporated under reduced pressure with ethyl acetate, repeatedly, to remove hydrogen chloride. The residue was triturated with ether to provide the title compound as a colorless powder, which was used for the next reaction directly.

EXAMPLE 66

The preparation of 3S-[2-Boc-Ala-Arg(Tos)-Pro-Ala-Lys(ClZ)]-1,2,3,4-tetrahydro-β-carboline-3-carboxylic acid benzyl ester (SEQ ID NO: 13)

At 0° C. the solution of 280 mg (0.915 mmol) of 3S-1,2,3,4-tetrahydro-β-carboline-3-carboxylic acid benzyl ester in 25 ml of anhydrous tetrahydrofuran was adjusted to pH 9, to which the pre-cold solution of 860 mg (0.893 mmol) of Boc-Ala-Arg(Tos)-Pro-Ala-Lys(ClZ)-OH (SEQ ID NO: 13),120 mg (0.889 mmol) of 1-hydroxybenzotriazole and 190 mg (0.922 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of Boc-Ala-Arg(Tos)-Pro-Ala-Lys(ClZ)-OH (SEQ ID NO: 13). The resulted precipitates of N,N-dicyclohexylurea were filtrated and the filtrate was diluted with 80 ml of ethyl acetate. The solution obtained was washed successively with saturated $NaCO_3$ in water (50 ml×3), saturated NaCl in water (50 ml×3) and $KHSO_4$ in water (5%. 30 ml×3). The separated ethyl acetate layer was dried with anhydrous $MgSO_4$, and then evaporated to provide 850 mg (76%) of the title compound as a colorless powder. Mp 109–110° C., FAB-MS (m/e) 1253.9 $[M+H]^+$, 1277.3 $[M+Na]^+$.

EXAMPLE 67

The preparation of 3S-(2-Boc)-1,2,3,4-tetrahydro-β-carboline-3-carboxyl-Ala-Arg(Tos)-Pro-Ala-Lys (ClZ)-OBzl (SEQ ID NO: 13)

At 0° C. the solution of 280 mg (0.283 mmol) of HCl Ala-Arg(Tos)-Pro-Ala-Lys(ClZ)-OBzl (SEQ ID NO: 13) in 15 ml of anhydrous tetrahydrofuran was adjusted to pH 9, to which the pre-cold solution of 100 mg (0.316 mmol) of 3S-(2-Boc)-1,2,3,4-tetrahydro-β-carboline-3-carboxylic acid, 43 mg (0.318 mmol) of 1-hydroxybenzotriazole and 65 mg (0.315 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of HCl Ala-Arg(Tos)-Pro-Ala-Lys(ClZ)-OBzl (SEQ ID NO: 13). The resulted precipitates of N,N-dicyclohexylurea were filtrated and the filtrate was diluted with 80 ml of ethyl acetate. The solution obtained was washed successively with saturated $NaCO_3$ in water (50 ml×3), saturated NaCl in water (50 ml×3) and $KHSO_4$ in water (5%, 30 ml×3). The separated ethyl acetate layer was dried with anhydrous $MgSO_4$, and then evaporated to provide 300 mg (84.7%) of the title compound as a colorless powder. Mp 129–31° C., FAB-MS (m/e) 1252.1 $[M+H]^+$, 1274.0 $[M+Na]^+$, 1152.7$[M-Boc]^+$.

EXAMPLE 68

The preparation of 3S-[2-Boc-Gly-Arg(Tos)-Pro-Ala-Lys(ClZ)]-1,2,3,4-tetrahydro-β-carboline-3-carboxylic acid benzyl ester (SEQ ID NO: 14)

At 0° C. the solution of 60 mg (0.196 mmol) of 3S-1,2,3,4-tetrahydro-β-carboline-3-carboxylic acid benzyl ester in 25 ml of anhydrous tetrahydrofuran was adjusted to pH 9, to which the pre-cold solution of 180 mg (0.190 mmol) of Boc-Gly-Arg(Tos)-Pro-Ala-Lys(ClZ)-OH (SEQ ID NO: 14), 25 mg (0.185 mmol) of 1-hydroxybenzotriazole and 40 mg (0.194 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of Boc-Ala-Arg(Tos)-Pro-Ala-Lys(ClZ)-OH (SEQ ID NO: 13). The resulted precipitates of N,N-dicyclohexylurea were filtrated and the filtrate was diluted with 80 ml of ethyl acetate. The solution obtained was washed successively with saturated $NaCO_3$ in water (50 ml×3), saturated NaCl in water (50 ml×3) and $KHSO_4$ in water (5%, 30 ml×3). The separated ethyl acetate layer was dried with anhydrous $MgSO_4$, and then evaporated to provide 220 mg (93%) of the title compound as a colorless powder. Mp 118–9° C., FAB-MS (m/e) 1239.4 $[M+H]^+$, 1275.7 $[M+K]^+$.

EXAMPLE 69

The preparation of 3S-(2-Boc)-1,2,3,4-tetrahydro-β-carboline-3-carboxyl-Gly-Arg(Tos)-Pro-Ala-Lys (ClZ)-OBzl (SEQ ID NO: 14)

At 0° C. the solution of 300 mg (0.307 mmol) of HCl Gly-Arg(Tos)-Pro-Ala-Lys(ClZ)-OBzl (SEQ ID NO: 14) in 15 ml of anhydrous tetrahydrofuran was adjusted to pH 9, to which the pre-cold solution of 115 mg (0.364 mmol) of 3S-(2-Boc)-1,2,3,4-tetrahydro-β-carboline-3-carboxylic acid, 50 mg (0.370 mmol) of 1-hydroxybenzotriazole and 75 mg (0.364 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of HCl Gly-Arg(Tos)-Pro-Ala-Lys(ClZ)-OBzl (SEQ ID NO: 14). The resulted precipitates of N,N-dicyclohexylurea were filtrated and the filtrate was diluted with 80 ml of ethyl acetate. The solution obtained was washed successively with saturated $NaCO_3$ in water (50 ml×3), saturated NaCl in water (50 ml×3) and $KHSO_4$ in water (5%, 30 ml×3). The separated ethyl acetate layer was dried with anhydrous $MgSO_4$, and then evaporated to provide 270 mg (72%) of the title compound as a colorless powder. Mp 114–6° C., FAB-MS (m/e) 1239.1 $[M+H]^+$, 1261.4 $[M+Na]^+$, 1137.9 $[M-Boc]^+$, 1373.9 $[M+Cs]^+$.

EXAMPLE 70

The preparation of 3S-[2-Boc-Lys(ClZ)-Arg(Tos)-Pro-Ala-Lys-(ClZ)]-1,2,3,4-tetrahydro-β-carbo-line-3-carboxylic acid benzyl ester (SEQ ID NO: 15)

At 0° C. the solution of 53 mg (0.173 mmol) of 3S-1,2,3,4-tetrahydro-β-carboline-3-carboxylic acid benzyl ester in 25 ml of anhydrous tetrahydrofuran was adjusted to pH 9, to which the pre-cold solution of 200 mg (0.1683 mmol) of Boc-Lys(ClZ)-Arg(Tos)-Pro-Ala-Lys(ClZ)-OH (SEQ ID NO: 15), 23 mg (0.170 mmol) of 1-hydroxybenzotriazole and 36 mg (0.175 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of Boc-Lys(ClZ)-Arg(Tos)-Pro-Ala-Lys(ClZ)-OH (SEQ ID NO: 15). The resulted precipitates of N,N-dicyclohexylurea were filtrated and the filtrate was diluted with 80 ml of ethyl acetate. The solution obtained was washed successively with saturated $NaCO_3$ in water (50 ml×3), saturated NaCl in water (50 ml×3) and $KHSO_4$ in water (5%, 30 ml×3). The separated ethyl acetate layer was dried with anhydrous $MgSO_4$, and then evaporated to provide 200 mg (80%) of the title compound as a colorless powder. Mp 94–6° C., FAB-MS (m/e) $[M+H]^+$ 1477.

EXAMPLE 71

The preparation of 3S-(2-Boc)-1,2,3,4-tetrahydro-β-carboline-3-carboxyl-Lys(ClZ)-Arg(Tos)-Pro-Ala-Lys(ClZ)-OBzl (SEQ ID NO: 15)

At 0° C. the solution of 330 mg (0.271 mmol) of HCl Lys(ClZ)-Arg(Tos)-Pro-Ala-Lys(ClZ)-OBzl (SEQ ID NO: 15) in 15 ml of anhydrous tetrahydrofuran was adjusted to pH 9, to which the pre-cold solution of 90 mg (0.285 mmol) of 3S-(2-Boc)-1,2,3,4-tetrahydro-β-carboline-3-carboxylic acid, 40 mg (0.296 mmol) of 1-hydroxybenzotriazole and 60 mg (0.291 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of HCl Lys(ClZ)-Arg(Tos)-Pro-Ala-Lys (ClZ)-OBzl (SEQ ID NO: 15). The resulted precipitates of N,N-dicyclohexylurea were filtrated and the filtrate was diluted with 80 ml of ethyl acetate. The solution obtained was washed successively with saturated $NaCO_3$ in water (50 ml×3), saturated NaCl in water (50 ml×3) and $KHSO_4$ in water (5%, 30 ml×3). The separated ethyl acetate layer was dried with anhydrous MgSO$_4$, and then evaporated to provide 320 mg (79%) of the title compound as a colorless powder. Mp 86–88° C., FAB-MS (m/e) 1477[M+H]$^+$.

EXAMPLE 72

The preparation of 3S-[2-Boc-Gln-Arg(Tos)-Pro-Ala-Lys(ClZ)]-1,2,3,4-tetrahydro-β-carboline-3-carboxylic acid benzyl ester (SEQ ID NO: 16)

At 0° C. the solution of 180 mg (0.570 mmol) of 3S-1,2,3,4-tetrahydro-β-carboline-3-carboxylic acid benzyl ester in 25 ml of anhydrous tetrahydrofuran was adjusted to pH 9, to which the pre-cold solution of 540 mg (0.529 mmol) of Boc-Gln-Arg(Tos)-Pro-Ala-Lys(ClZ)-OH (SEQ ID NO: 16), 70 mg (0.52 mmol) of 1-hydroxybenzotriazole and 120 mg (0.582 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of Boc-Gln-Arg(Tos)-Pro-Ala-Lys(ClZ)-OH (SEQ ID NO: 16). The resulted precipitates of N,N-dicyclohexylurea were filtrated and the filtrate was diluted with 80 ml of ethyl acetate. The solution obtained was washed successively with saturated NaCO$_3$ in water (50 ml×3), saturated NaCl in water (50 ml×3) and KHSO$_4$ in water (5%, 30 ml×3). The separated ethyl acetate layer was dried with anhydrous MgSO$_4$, and then evaporated to provide 550 mg (79%) of the title compound as a colorless powder. Mp 118–120° C., FAB-MS (m/e) 1311.4 [M+H]$^+$, 1333.4 [M+Na]$^+$, 1209.1 [M-Boc]$^+$.

EXAMPLE 73

The preparation of 3S-(2-Boc)-1,2,3,4-tetrahydro-β-carbo-line-3-carboxyl-Gln-Arg(Tos)-Pro-Ala-Lys(ClZ)-OBzl (SEQ ID NO: 16)

At 0° C. the solution of 440 mg (0.421 mmol) of HCl Gln-Arg(Tos)-Pro-Ala-Lys(ClZ)-OBzl (SEQ ID NO: 16) in 15 ml of anhydrous tetrahydrofuran was adjusted to pH 9, to which the pre-cold solution of 140 mg (0.443 mmol) of 3S-(2-Boc)-1,2,3,4-tetrahydro-β-carboline-3-carboxylic acid, 60 mg (0.444 mmol) of 1-hydroxybenzotriazole and 90 mg (0.437 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of HCl Gln-Arg(Tos)-Pro-Ala-Lys(ClZ)-OBzl (SEQ ID NO: 16). The resulted precipitates of N,N-dicyclohexylurea were filtrated and the filtrate was diluted with 80 ml of ethyl acetate. The solution obtained was washed successively with saturated NaCO$_3$ in water (50 ml×3), saturated NaCl in water (50 ml×3) and KHSO$_4$ in water (5%, 30 ml×3). The separated ethyl acetate layer was dried with anhydrous MgSO$_4$, and then evaporated to provide 250 mg (45%) of the title compound as a colorless powder. Mp 126–8° C., FAB-MS (m/e) 1309.3 [M+H]$^+$, 1209.3 [M-Boc]$^+$.

EXAMPLE 74

The preparation of 3S-[2-Boc-Asn-Arg(Tos)-Pro-Ala-Lys(ClZ)]-1,2,3,4-tetrahydro-β-carboline-3-carboxylic acid benzyl ester (SEQ ID NO: 17)

At 0° C. the solution of 13 mg (42.48 mmol) of 3S-1,2,3,4-tetrahydro-β-carboline-3-carboxylic acid benzyl ester in 25 ml of anhydrous tetrahydrofuran was adjusted to pH 9, to which the pre-cold solution of 40 mg (39.76 mmol) of Boc-Asn-Arg(Tos)-Pro-Ala-Lys(ClZ)-OH (SEQ ID NO: 17), 6 mg (44.44 mol) of 1-hydroxybenzotriazole and 9 mg (43.69 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of Boc-Asn-Arg(Tos)-Pro-Ala-Lys(ClZ)-OH (SEQ ID NO: 17). The resulted precipitates of N,N-dicyclohexylurea were filtrated and the filtrate was diluted with 80 ml of ethyl acetate. The solution obtained was washed successively with saturated NaCO$_3$ in water (50 ml×3), saturated NaCl in water (50 ml×3) and KHSO$_4$ in water (5%, 30 ml×3). The separated ethyl acetate layer was dried with anhydrous MgSO$_4$, and then evaporated to provide 40 mg (77%) of the title compound as a colorless powder. Mp 115–7° C., FAB-MS (m/e) 1553[M+8CH$_3$OH+H]$^+$.

EXAMPLE 75

The preparation of 3S-(2-Boc)-1,2,3,4-tetrahydro-β-carboline-3-carboxyl-Asn-Arg(Tos)-Pro-Ala-Lys(ClZ)-OBzl (SEQ ID NO: 17)

At 0° C. the solution of 94 mg (0.091 mmol) of HCl Asn-Arg(Tos)-Pro-Ala-Lys(ClZ)-OBzl (SEQ ID NO: 17) in 15 ml of anhydrous tetrahydrofuran was adjusted to pH 9, to which the pre-cold solution of 30 mg (0.095 mmol) of 3S-(2-Boc)-1,2,3,4-tetrahydro-β-carboline-3-carboxylic acid, 20 mg (0.148 mmol) of 1-hydroxybenzotriazole and 25 mg (0.121 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of HCl Asn-Arg(Tos)-Pro-Ala-Lys(ClZ)-OBzl (SEQ ID NO: 17). The resulted precipitates of N,N-dicyclohexylurea were filtrated and the filtrate was diluted with 80 ml of ethyl acetate. The solution obtained was washed successively with saturated NaCO$_3$ in water (50 ml×3), saturated NaCl in water (50 ml×3) and KHSO$_4$ in water (5%, 30 ml×3). The separated ethyl acetate layer was dried with anhydrous MgSO$_4$, and then evaporated to provide 50 mg (42%) of the title compound as a colorless powder. Mp 123–126° C., FAB-MS (m/e) 1351[M+C$_4$H$_9$]$^+$.

EXAMPLE 76

The preparation of 3S-[2-Boc-Arg(Tos)-Arg(Tos)-Pro-Ala-Lys-(ClZ)]-1,2,3,4-tetrahydro-β-carboline-3-carboxylic acid benzyl ester (SEQ ID NO: 18)

At 0° C. the solution of 120 mg (0.392 mmol) of 3S-1,2,3,4-tetrahydro-β-carboline-3-carboxylic acid benzyl ester in 25 ml of anhydrous tetrahydrofuran was adjusted to pH 9, to which the pre-cold solution of 420 mg (0.349 mmol) of Boc-Arg(Tos)-Arg(Tos)-Pro-Ala-Lys(ClZ)-OH (SEQ ID NO: 18), 50 mg (0.370 mmol) of 1-hydroxybenzotriazole and 80 mg (0.388 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of Boc-Arg(Tos)-Arg(Tos)-Pro-Ala-Lys(ClZ)-OH (SEQ ID NO: 18). The resulted precipitates of N,N-dicyclohexylurea were filtrated and the filtrate was diluted with 80 ml of ethyl acetate. The solution obtained was washed successively with saturated NaCO$_3$ in water (50 ml×3), saturated NaCl in water (50 ml×3) and KHSO$_4$ in water (5%, 30 ml×3). The separated ethyl acetate layer was dried with anhydrous MgSO$_4$, and then evaporated to provide 230 mg (44%) of the title compound as a colorless powder. Mp 96–99° C., FAB-MS (m/e) 1491[M+H]$^+$.

EXAMPLE 77

The preparation of 3S-(2-Boc)-1,2,3,4-tetrahydro-β-carbo-line-3-carboxyl-Arg(Tos)-Arg(Tos)-Pro-Ala-Lys(ClZ)-OBzl (SEQ ID NO: 18)

At 0° C. the solution of 665 mg (0.541 mmol) of HCl Arg(Tos)-Arg(Tos)-Pro-Ala-Lys(ClZ)-OBzl (SEQ ID NO: 18) in 15 ml of anhydrous tetrahydrofuran was adjusted to pH 9, to which the pre-cold solution of 180 mg (0.570 mmol) of 3S-(2-Boc)-1,2,3,4-tetrahydro-β-carboline-3-carboxylic acid, 80 mg (0.592 mmol) of 1-hydroxybenzotriazole and 120 mg (0.582 mmol) of dicyclohexylcarbodiimide in 20 ml of anhydrous tetrahydrofuran was added. The reaction mixture was stirred at 0° C. for 2 h and at room temperature for 6 h and TLC (chloroform/methanol, 10:1) indicated complete disappearance of HCl Arg(Tos)-Arg(Tos)-Pro-Ala-Lys(ClZ)-OBzl (SEQ ID NO: 18). The resulted precipitates of N,N-dicyclohexylurea were filtrated and the filtrate was diluted with 80 ml of ethyl acetate. The solution obtained was washed successively with saturated NaCO$_3$ in water (50 ml×3), saturated NaCl in water (50 ml×3) and KHSO$_4$ in water (5%, 30 ml×3). The separated ethyl acetate layer was dried with anhydrous MgSO$_4$, and then evaporated to provide 350 mg (43%) of the title compound as a colorless powder. Mp 120–122° C., FAB-MS (m/e) 1492[M+H]$^+$.

EXAMPLE 78

The preparation of 3S-1,2,3,4-tetrahydro-β-carbo-line-3-Car-boxyl-Ala-Arg-Pro-Ala-Lys-OH (11) (SEQ ID NO: 1)

The solution of 100 mg (0.080 mmol) of 3S-(2-Boc)-1,2,3,4-tetrahydro-β-carboline-3-carboxyl-Ala-Arg(Tos)-Pro-Ala-Lys(ClZ)-OBzl (SEQ ID NO: 13), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 245 mg (76%) of the title compound. Mp. 220–224° C. (decomp.), FAB-MS (m/e) 740 [M+H]$^+$.

EXAMPLE 79

The preparation of 3S-1,2,3,4-tetrahydro-β-carbo-line-3-carbo-xyl-Gly-Arg-Pro-Ala-Lys-OH (12) (SEQ ID NO: 19)

The solution of 250 mg (0.330 mmol) of 3S-(2-Boc)-1,2,3,4-tetrahydro-β-carboline-3-carboxyl-Gly-Arg(Tos)-Pro-Ala-Lys(ClZ)-OBzl (SEQ ID NO: 14), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 45 mg (75%) of the title compound. Mp. 210–213° C., FAB-MS (m/e) 726[M+H]$^+$.

EXAMPLE 80

The preparation of 3S-1,2,3,4-tetrahydro-β-carbo-line-3-carbo-xyl-Lys-Arg-Pro-Ala-Lys-OH (13) (SEQ ID NO: 5)

The solution of 290 mg (0.196 mmol) of 3S-(2-Boc)-1,2,3,4-tetrahydro-β-carboline-3-carboxyl-Lys(ClZ)-Arg(Tos)-Pro-Ala-Lys(ClZ)-OBzl (SEQ ID NO: 15), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 130 mg (83%) of the title compound. Mp. 206–208° C., FAB-MS (m/e) 797[M+H]$^+$.

EXAMPLE 81

The preparation of 3S-1,2,3,4-tetrahydro-β-carbo-line-3-car-boxyl-Gln-Arg-Pro-Ala-Lys-OH (14) (SEQ ID NO: 4)

The solution of 250 mg (0.330 mmol) of 3S-(2-Boc)-1,2,3,4-tetrahydro-β-carboline-3-carboxyl-Gln-Arg(Tos)-Pro-Ala-Lys(ClZ)-OBzl (SEQ ID NO: 16), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 80 mg (58%) of the title compound. Mp. 218–220° C., FAB-MS (m/e) 797[M+H]$^+$.

EXAMPLE 82

The preparation of 3S-1,2,3,4-tetrahydro-β-carbo-line-3-carbo-xyl-Asn-Arg-Pro-Ala-Lys-OH (15) (SEQ ID NO: 6)

The solution of 250 mg (0.330 mmol) of 3S-(2-Boc)-1,2,3,4-tetrahydro-β-carboline-3-carboxyl-Asn-Arg(Tos)-Pro-Ala-Lys(ClZ)-OBzl (SEQ ID NO: 17), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 80 mg (58%) of the title compound. Mp. 211–214° C., FAB-MS (m/e) 784[M+H]$^+$.

EXAMPLE 83

The preparation of 3S-(2-Arg-Arg-Pro-Ala-Lys)-1,2,3,4-tetra-hydro-β-carboline-3-carboxylic acid (16) (SEQ ID NO: 20)

The solution of 200 mg (0.134 mmol) of 3S-[2-Boc-Arg(Tos)-Arg(Tos)-Pro-Ala-Lys(ClZ)]-1,2,3,4-tetrahydro-β-carboline-3-carboxylic acid benzyl ester (SEQ ID NO: 18), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 80 mg (72%) of the title compound. Mp. 208–212° C. (decomp.), FAB-MS (m/e) 825 [M+H]$^+$.

EXAMPLE 84

The preparation of 3S-1,2,3,4-tetrahydro-β-carboline-3-car-boxyl-Ala-Arg-Pro-Ala-OH (17) (SEQ ID NO: 2)

The solution of 440 mg (0.373 mmol) of 3S-(2-Boc)-1,2,3,4-tetrahydro-β-carboline-3-carboxyl-Ala-Arg(Tos)-Pro-Ala-OBzl (SEQ ID NO: 7), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 240 mg (96%) of the title compound. Mp. 240–245° C. (decomp.), FAB-MS (m/e) 613 [M+H]$^+$.

EXAMPLE 85

The preparation of 3S-1,2,3,4-tetrahydro-β-carboline-3-carbo-xyl-Ala-Arg-Pro-OH (18)

The solution of 120 mg (0.230 mmol) of 3S-(2-Boc)-1,2,3,4-tetrahydro-β-carboline-3-carboxyl-Ala-Arg(Tos)-Pro-OBzl, 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 40 mg (55%) of the title compound. Mp. 186–188° C., FAB-MS (m/e) 542[M+H]$^+$.

EXAMPLE 86

The preparation of 3S-1,2,3,4-tetrahydro-β-carboline-3-carboxyl-Arg-Pro-Ala-Lys-OH (19) (SEQ ID NO: 3)

The solution of 440 mg (0.373 mmol) of 3S-(2-Boc)-1,2,3,4-tetrahydro-β-carboline-3-carboxyl-Arg(Tos)-Pro-Ala-Lys(ClZ)-OBzl (SEQ ID NO: 12), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 240 mg (96%) of the title compound. Mp. 240–245° C. (decomp.), FAB-MS (m/e) 669 [M+H]$^+$.

EXAMPLE 87

The preparation of 3S-1,2,3,4-tetrahydro-β-carboline-3-car-boxyl-Pro-Ala-Lys-OH (20)

The solution of 200 mg (0.230 mmol) of 3S-(2-Boc)-1,2,3,4-tetrahydro-β-carboline-3-carboxylPro-Ala-Lys(ClZ)-OBzl, 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 70 mg (67%) of the title compound. Mp. 186–188° C., FAB-MS (m/e) 513[M+H]$^+$.

EXAMPLE 88

The preparation of 3S-(2-Ala-Arg-Pro-Ala-Lys)-1,2,3,4-tetra-hydro-β-carboline-3-carboxylic acid (21) (SEQ ID NO: 1)

The solution of 100 mg (0.080 mmol) of 3S-[2-Boc-Ala-Arg(Tos)-Pro-Ala-Lys(ClZ)]-1,2,3,4-tetrahydro-β-carboline-3-carboxylic acid benzyl ester (SEQ ID NO: 13), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 50 mg (84.6%) of the title compound. Mp. 236–239° C. (decomp.), ESI-MS (m/e) 740 [M+H]$^+$.

EXAMPLE 89

The preparation of 3S-(2-Gly-Arg-Pro-Ala-Lys)-1,2, 3,4-tetrahy-dro-β-carboline-3-carboxylic acid (22) (SEQ ID NO: 19)

The solution of 100 mg (0.081 mmol) of 3S-[2-Boc-Gly-Arg(Tos)-Pro-Ala-Lys(ClZ)]-1,2,3,4-tetrahydro-β-carboline-3-carboxylic acid benzyl ester (SEQ ID NO: 14), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 50 mg (85%) of the title compound. Mp. 214–218° C., FAB-MS (m/e) 726[M+H]$^+$.

EXAMPLE 90

The preparation of 3S-(2-Lys-Arg-Pro-Ala-Lys)-1,2, 3,4-tetra-hydro-β-carboline-3-carboxylic acid (23) (SEQ ID NO: 5)

The solution of 185 mg (0.125 mmol) of 3S-[2-Boc-Lys(ClZ)-Arg(Tos)-Pro-Ala-Lys(ClZ)]-1,2,3,4-tetrahydro-β-carboline-3-carboxylic acid benzyl ester (SEQ ID NO: 15), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 90 mg (87%) of the title compound. Mp. 250–260° C., FAB-MS (m/e) 797[M+H]$^+$.

EXAMPLE 91

The preparation of 3S-(2-Gln-Arg-Pro-Ala-Lys)-1,2, 3,4-tetra-hydro-β-carboline-3-carboxylic acid (24) (SEQ ID NO: 4)

The solution of 280 mg (0.200 mmol) of 3S-[2-Boc-Gln-Arg(Tos)-Pro-Ala-Lys(ClZ)]-1,2,3,4-tetrahydro-β-carboline-3-carboxylic acid benzyl ester (SEQ ID NO: 16), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 130 mg (81%) of the title compound. Mp. 230–232° C. (decomp.), FAB-MS (m/e) 798 [M+H]$^+$.

EXAMPLE 92

The preparation of 3S-(2-Asn-Arg-Pro-Ala-Lys)-1, 2,3,4-tetra-hydro-β-carboline-3-carboxylic acid (25) (SEQ ID NO: 6)

The solution of 200 mg (0.182 mmol) of 3S-[2-Boc-Asn-Arg(Tos)-Pro-Ala-Lys(ClZ)]-1,2,3,4-tetrahydro-β-carboline-3-carboxylic acid benzyl ester (SEQ ID NO: 17), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 70 mg (51%) of the title compound. Mp. 198–200° C., FAB-MS (m/e) 783[M+H]$^+$.

EXAMPLE 93

The preparation of 3S-1,2,3,4-tetrahydro-β-carboline-3-car-boxyl-Arg-Arg-Pro-Ala-Lys-OH (26) (SEQ ID NO: 20)

The solution of 340 mg (0.228 mmol) of 3S-(2-Boc)-1,2,3,4-tetrahydro-β-carboline-3-carboxyl-Arg(Tos)-Arg(Tos)-Pro-Ala-Lys(ClZ)-OBzl (SEQ ID NO: 18), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 130 mg (69%) of the title compound. Mp. 238–240° C. (decomp.), FAB-MS (m/e) 825 [M+H]$^+$.

EXAMPLE 94

The preparation of 3S-(2-Ala-Arg-Pro-Ala)-1,2,3,4-tetrahydro-β-carboline-3-carboxylic acid (27) (SEQ ID NO: 2)

The solution of 220 mg (0.186 mmol) of 3S-[2-Boc-Ala-Arg(Tos)-Pro-Ala]-1,2,3,4-tetrahydro-β-carboline-3-carboxylic acid benzyl ester (SEQ ID NO: 7), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 60 mg (48%) of the title compound. Mp. 114–116° C., FAB-MS (m/e) 613[M+H]$^+$.

EXAMPLE 95

The preparation of 3S-(2-Ala-Arg-Pro)-1,2,3,4-tetrahydro-β-carboline-3-carboxylic acid (28)

The solution of 120 mg (0.230 mmol) of 3S-[2-Boc-Ala-Arg(Tos)-Pro]-1,2,3,4-tetrahydro-β-carboline-3-carboxylic acid benzyl ester, 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 250 mg (85%) of the title compound. Mp. 130–134° C., FAB-MS (m/e) 542[M+H]$^+$.

EXAMPLE 96

The preparation of 3S-(2-Arg-Pro-Ala-Lys)-1,2,3,4-tetrahydro-β-carboline-3-carboxylic acid (29) (SEQ ID NO: 3)

The solution of 220 mg (0.186 mmol) of 3S-[2-Boc-Arg(Tos)-Pro-Ala-Lys(ClZ)]-1,2,3,4-tetrahydro-β-carboline-3-carboxylic acid benzyl ester (SEQ ID NO: 12), 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 60 mg (48%) of the title compound. Mp. 114–116° C., FAB-MS (m/e) 669[M+H]$^+$.

EXAMPLE 97

The preparation of 3S-(2-Pro-Ala-Lys)-1,2,3,4-tetrahydro-β-carboline-3-carboxylic acid (30)

The solution of 500 mg (0.330 mmol) of 3S-[2-Boc-Pro-Ala-Lys(ClZ)]-1,2,3,4-tetrahydro-β-carboline-3-carboxylic acid benzyl ester, 1 ml of anisole and 2 ml of HF was stirred at 0° C. for 2 h. The reaction mixture was evaporated under reduced pressure to remove HF. To the residue 2 ml of HF were added and the solution was stirred at 0° C. for another 1 h. The reaction mixture was evaporated under reduced pressure to remove HF. The residue was triturated with ether and the resulted solid was purified on the Sephadex G-10 column. The collected fractions were lyophilized to provide of 250 mg (85%) of the title compound. Mp. 130–134° C., FAB-MS (m/e) 669[M+H]$^+$.

EXAMPLE 98

In Vitro Fibrinolytic Lysis

The plates were prepared by mixing equal volumes of 0.3% rabbit fibrinogen and 0.95% agarose solutions, both dissolved in 50 mM of barbital buffer (pH 7.8, contained 1.66 mM of $CaCl_2$, 0.68 mM of $MgCl_2$ and 93.96 mM of NaCl)[6]. The fibrinogen-agarose mixture was coagulated with 100 ml thrombin (100 IU: ml) in the plastic dishes (its diameter is 90 mm and the depth of the fibrin plate is 1 mm). After 30 min at 4° C. an adequate number of wells, 5 mm in diameter, were perforated. To determine fibrinolytic activity 30l aliquots of the tested pseudopeptides were added to each well, the plate was incubated, and areas of lysis were quantified as described for the regular fibrin plates. The quantified lysis areas of the regular fibrin plates for the tested pseudopeptides are listed in Table 1.

TABLE 1

| Effect of the pseudopeptides on fibrin plate | | |
| --- | --- | --- |
| Compd. | Dosage (μg) | $\bar{x}$ ± SD (mm$^2$) |
| NS | | 21.01 ± 9.26 |
| UK | 5 IU | 122.19 ± 11.90$^a$ |
| 1 | 1.4 | 119.12 ± 12.44$^a$ |
| 2 | 1.4 | 125.90 ± 11.15$^a$ |
| 3 | 1.6 | 38.99 ± 9.06 |
| 4 | 1.6 | 136.28 ± 10.62$^a$ |
| 5 | 1.6 | 22.66 ± 9.46 |
| 6 | 1.7 | 33.77 ± 10.05 |
| 7 | 1.3 | 125.33 ± 10.10$^a$ |
| 8 | 0.8 | 138.06 ± 9.39$^a$ |
| 9 | 0.9 | 23.16 ± 9.05 |
| 10 | 1.1 | 31.01 ± 9.26 |
| 11 | 2.0 | 24.10 ± 10.16 |
| 12 | 1.9 | 23.53 ± 9.74 |
| 13 | 2.1 | 24.01 ± 10.05 |
| 14 | 2.1 | 22.89 ± 10.02 |
| 15 | 2.1 | 23.21 ± 9.74 |
| 16 | 2.2 | 24.19 ± 10.08 |
| 17 | 1.6 | 23.44 ± 10.18 |
| 18 | 1.4 | 23.88 ± 10.04 |
| 19 | 1.8 | 20.33 ± 9.28 |
| 20 | 1.4 | 19.41 ± 11.71 |
| 21 | 1.9 | 119.70 ± 10.71$^a$ |
| 22 | 2.0 | 125.90 ± 11.15$^a$ |
| 23 | 2.1 | 19.87 ± 9.58 |
| 24 | 2.1 | 133.89 ± 9.99$^a$ |
| 25 | 2.1 | 20.84 ± 10.77 |
| 26 | 2.2 | 24.00 ± 12.01 |
| 27 | 1.6 | 23.32 ± 9.99 |
| 28 | 1.4 | 21.21 ± 11.11 |
| 29 | 1.8 | 126.55 ± 9.98$^a$ |
| 30 | 1.8 | 139.39 ± 9.52$^a$ | n = 6;
$^a$compare to NS p < 0.001

EXAMPLE 99

In Vitro Euglobulin Clot Lysis Time

The rabbit euglobulin fraction was prepared according to the literature[6]. Plasma diluted 1.20 in distilled water was precipitated at pH 5.7 with acetic acid (0.25%). After 30 min at 4° C. the suspension was centrifuged at 2000 g for 15 min and the precipitate was resuspended to the initial plasma volume with 50 mM barbital buffer (pH 7.8, contained 1.66 mM of $CaCl_2$, 0.68 mM of $MgCl_2$ and 93.96 mM of NaCl). Euglobulin clot lysis time (ECLT) of the tested pseudopeptide was measured using a 96 well microtiter plate[7] and the data are listed in Table 2.

TABLE 2

Euglobulin clot lysis time of the pseudopeptides

| Compd. | Dosage (μg) | x̄ ± SD(min) |
|---|---|---|
| NS |  | 200.01 ± 15.26 |
| UK | 5 IU | 122.19 ± 20.90[a] |
| 1 | 2.0 | 90.12 ± 17.64[a,b] |
| 2 | 2.1 | 89.90 ± 20.05[a,b] |
| 3 | 2.4 | 221.28 ± 23.46 |
| 4 | 2.4 | 86.28 ± 20.46[a,b] |
| 5 | 2.3 | 212.88 ± 29.66 |
| 6 | 2.5 | 213.31 ± 27.75 |
| 7 | 1.9 | 85.22 ± 20.40[a,b] |
| 8 | 1.3 | 80.68 ± 20.34[a,b] |
| 9 | 1.4 | 203.81 ± 29.50 |
| 10 | 1.6 | 214.01 ± 28.26 |
| 11 | 2.9 | 204.01 ± 32.61 |
| 12 | 2.9 | 213.35 ± 29.47 |
| 13 | 3.2 | 214.11 ± 32.67 |
| 14 | 3.2 | 212.98 ± 28.42 |
| 15 | 3.1 | 213.12 ± 29.47 |
| 16 | 3.2 | 204.11 ± 32.87 |
| 17 | 2.2 | 213.55 ± 30.47 |
| 18 | 2.2 | 203.66 ± 30.44 |
| 19 | 2.7 | 213.56 ± 29.95 |
| 20 | 2.0 | 209.31 ± 31.57 |
| 21 | 2.9 | 119.70 ± 23.71[a] |
| 22 | 2.9 | 98.02 ± 25.21[a] |
| 23 | 3.2 | 213.98 ± 29.45 |
| 24 | 3.2 | 96.88 ± 29.21[1a] |
| 25 | 3.1 | 217.27 ± 30.57 |
| 26 | 3.2 | 214.80 ± 32.96 |
| 27 | 2.4 | 203.89 ± 29.67 |
| 28 | 2.2 | 213.23 ± 31.58 |
| 29 | 2.7 | 104.40 ± 27.51[a] |
| 30 | 6.7 | 96.56 ± 30.42[a] | n = 6;
[a]compare to NS p < 0.001;
[b]compare to UK, p < 0.05

EXAMPLE 100

In Vivo Thrombolytic Activities[8]

Male Wistar rats weighing 200–300 g (purchased from Animal Center of Peking University) were anesthetized with pentobarbital sodium (80.0 mg/kg, ip). The right carotid artery and left vein jugular of the animals were separated. To the glass tube filled with artery blood (1.0 ml) from the right carotid artery of the animal a stainless steel filament helix (15 circles; L, 15 mm; D, 1.0 mm) was put immediately. After 15 minutes the helix with thrombus was carefully taken out and weighted exactly, which was put into the middle polyethylene tube. The polyethylene tube was full with heparin sodium (50 IU/ml of NS) and one end was inserted into the left jugular vein. Heparin sodium was injected via the other end of the polyethylene tube as the anticoagulant, following which the tested pseudopeptide was injected. The blood was circulated through the polyethylene tube for 90 min, after which the helix was taken out and weighted accurately. The reduction of thrombolytic mass recorded are listed in Table 3.

TABLE 3

The reduction of thrombolytic mass

| Compd. | Dose (mg/kg) | x̄ ± SD (mg) |
|---|---|---|
| NS | 3 ml | 12.31 ± 2.57 |
| UK | 20000 IU | 22.10 ± 2.54[a] |
| 1 | 5.4 | 18.84 ± 3.18[1)2)] |
| 2 | 5.3 | 25.90 ± 2.05[1)] |
| 3 | 6.0 | 21.28 ± 3.46[1)2)] |
| 4 | 6.0 | 21.28 ± 3.46[1)2)] |
| 5 | 5.8 | 12.88 ± 2.66 |
| 6 | 6.3 | 13.31 ± 2.75 |
| 7 | 4.7 | 18.22 ± 2.40[a] |
| 8 | 3.1 | 23.68 ± 2.34[a] |
| 9 | 3.4 | 13.81 ± 2.50 |
| 10 | 4.2 | 14.01 ± 2.26 |
| 11 | 7.4 | 14.01 ± 2.61 |
| 12 | 7.3 | 13.35 ± 2.47 |
| 13 | 8.0 | 14.11 ± 2.67 |
| 14 | 8.0 | 12.98 ± 2.42 |
| 15 | 7.8 | 13.12 ± 2.47 |
| 16 | 8.2 | 14.11 ± 2.87 |
| 17 | 6.1 | 13.55 ± 2.47 |
| 18 | 5.4 | 13.66 ± 2.44 |
| 19 | 6.7 | 13.56 ± 2.45 |
| 20 | 5.1 | 1331 ± 2.57 |
| 21 | 7.4 | 19.7 ± 3.71[2)] |
| 22 | 7.3 | 24.02 ± 5.21[1)] |
| 23 | 8.0 | 13.98 ± 2.45 |
| 24 | 8.0 | 22.88 ± 9.21[1)] |
| 25 | 7.8 | 17.27 ± 3.57[2)] |
| 26 | 8.2 | 14.80 ± 2.96 |
| 27 | 6.1 | 13.89 ± 2.67 |
| 28 | 5.4 | 13.23 ± 2.58 |
| 29 | 6.7 | 24.40 ± 2.51[a,d] |
| 30 | 6.7 | 26.56 ± 2.42[b] | n = 10;
[a]compare to NS p < 0.001;
[b]compare to NS p < 0.01;
[c]compare to H-Arg-Pro-Ala-Lys-OH, p < 0.05;
[d]compare to H-Pro-Ala-Lys-OH and UK, p < 0.05

EXAMPLE 101

List of the Tested Peptides

H-Ala-Arg-Pro-Ala-Lys-OH (1) (SEQ ID NO: 1)
H-Gly-Arg-Pro-Ala-Lys-OH (2) (SEQ ID NO: 19)
H-Lys-Arg-Pro-Ala-Lys-OH (3) (SEQ ID NO: 5)
H-Gln-Arg-Pro-Ala-Lys-OH (4) (SEQ ID NO: 4)
H-Asn-Arg-Pro-Ala-Lys-OH (5) (SEQ ID NO: 6)
H-Arg-Arg-Pro-Ala-Lys-OH (6) (SEQ ID NO: 20)
H-Ala-Arg-Pro-Ala-OH (7) (SEQ ID NO: 2)
H-Ala-Arg-Pro-OH (8)
H-Arg-Pro-Ala-Lys-OH (9) (SEQ ID NO: 3)
H-Pro-Ala-Lys-OH (10)
3S-1,2,3,4-tetrahydro-β-carboline-3-carboxyl-Ala-Arg-Pro-Ala-Lys-OH (11) (SEQ ID NO: 1)
3S-1,2,3,4-tetrahydro-β-carboline-3-carboxyl-Gly-Arg-Pro-Ala-Lys-OH (12) (SEQ ID NO: 19)
3S-1,2,3,4-tetrahydro-β-carboline-3-carboxyl-Lys-Arg-Pro-Ala-Lys-OH (13) (SEQ ID NO: 5)
3S-1,2,3,4-tetrahydro-β-carboline-3-carboxyl-Gln-Arg-Pro-Ala-Lys-OH (14) (SEQ ID NO: 4)
3S-1,2,3,4-tetrahydro-β-carboline-3-carboxyl-Asn-Arg-Pro-Ala-Lys-OH (15) (SEQ ID NO: 6)
3S-1,2,3,4-tetrahydro-β-carboline-3-carboxyl-Arg-Arg-Pro-Ala-Lys-OH (16) (SEQ ID NO: 20)
3S-1,2,3,4-tetrahydro-β-carboline-3-carboxyl-Ala-Arg-Pro-Ala-OH (17) (SEQ ID NO: 2)
3S-1,2,3,4-tetrahydro-β-carboline-3-carboxyl-Ala-Arg-Pro-OH (18)

3S-1,2,3,4-tetrahydro-β-carboline-3-carboxyl-Arg-Pro-Ala-Lys-OH (19) (SEQ ID NO: 3)
3S-1,2,3,4-tetrahydro-β-carboline-3-carboxyl-Pro-Ala-Lys-OH (20)
3S-(2-Ala-Arg-Pro-Ala-Lys)-1,2,3,4-tetrahydro-β-carboline-3-carboxylic acid (21) (SEQ ID NO: 1)
3S-(2-Gly-Arg-Pro-Ala-Lys)-1,2,3,4-tetrahydro-β-carboline-3-carboxylic acid (22) (SEQ ID NO: 19)
3S-(2-Lys-Arg-Pro-Ala-Lys)-1,2,3,4-tetrahydro-β-carboline-3-carboxylic acid (23) (SEQ ID NO: 5)
3S-(2-Gln-Arg-Pro-Ala-Lys)-1,2,3,4-tetrahydro-β-carboline-3-carboxylic acid (24) (SEQ ID NO: 4)
3S-(2-Asn-Arg-Pro-Ala-Lys)-1,2,3,4-tetrahydro-β-carboline-3-carboxylic acid (25) (SEQ ID NO: 6)
3S-(2-Arg-Arg-Pro-Ala-Lys)-1,2,3,4-tetrahydro-β-carboline-3-carboxylic acid (26) (SEQ ID NO: 20)
3S-(2-Ala-Arg-Pro-Ala)-1,2,3,4-tetrahydro-β-carboline-3-carboxylic acid (27) (SEQ ID NO: 2)
3S-(2-Ala-Arg-Pro)-1,2,3,4-tetrahydro-β-carboline-3-carboxylic acid (28)
3S-(2-Arg-Pro-Ala-Lys)-1,2,3,4-tetrahydro-β-carboline-3-carboxylic acid (29) (SEQ ID NO: 3)
3S-(2-Pro-Ala-Lys)-1,2,3,4-tetrahydro-β-carboline-3-carboxylic acid (30)
3S-1,2,3,4-tetrahydro-β-carboline-3-carboxylic acid (31)

---

The invention claimed is:

1. A compound chosen from 3S-(2-Arg-Pro-Ala-Lys)-1,2,3,4,-tetrahydro-β-carboline-3-carboxylic acid and 3S-(2-Pro-Ala-Lys)-1,2,3,4,-tetrahydro-β-carboline-3-carboxylic acid.

2. The compound of claim 1, wherein the compound is 3S-(2-Arg-Pro-Ala-Lys)-1,2,3,4,-tetrahydro-β-carboline-3-carboxylic acid.

3. The compound of claim 1, wherein the compound is 3S-(2-Pro-Ala-Lys)-1,2,3,4,-tetrahydro-β-carboline-3-carboxylic acid.

4. A composition comprising a compound of claim 1 and a pharmaceutically acceptable carrier.

5. The composition of claim 1, wherein the compound is 3S-(2-Arg-Pro-Ala-Lys)-1,2,3,4,-tetrahydro-β-carboline-3-carboxylic acid.

6. The composition of claim 4, wherein the compound is 3S-(2-Pro-Ala-Lys)-1,2,3,4,-tetrahydro-β-carboline-3-carboxylic acid.

* * * * *

UNITED STATES PATENT AND TRADEMARK OFFICE
CERTIFICATE OF CORRECTION

PATENT NO. : 7,138,491 B2
APPLICATION NO. : 10/680293
DATED : November 21, 2006
INVENTOR(S) : Peng et al.

Page 1 of 1

It is certified that error appears in the above-identified patent and that said Letters Patent is hereby corrected as shown below:

Column 54, Claim 5, line 16, "claim 1," should read -- claim 4, --.

Signed and Sealed this

Sixth Day of March, 2007

JON W. DUDAS
*Director of the United States Patent and Trademark Office*

SEQUENCE LISTING

```
<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Arg Pro Ala Lys
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Arg Pro Ala
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Pro Ala Lys
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Arg Pro Ala Lys
1               5

<210> SEQ ID NO 5
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Arg Pro Ala Lys
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Arg Pro Ala Lys
 1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Arg(Tos)

<400> SEQUENCE: 7

Ala Arg Pro Ala
 1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Arg(Tos)
<220> FEATURE:
<221> NAME/KEY: MOD_RES
<222> LOCATION: (4)
<223> OTHER INFORMATION: Lys(Z)

<400> SEQUENCE: 8

Arg Pro Ala Lys
 1

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ala, Gly, Asn, Arg(Tos), Lys(Z), Arg, or Lys
<220> FEATURE:
```

```
<221> NAME/KEY: MOD_RES
<222> LOCATION: (2)
<223> OTHER INFORMATION: Arg(Tos)
<220> FEATURE:
<221> NAME/KEY: MOD_RES
<222> LOCATION: (5)
<223> OTHER INFORMATION: Lys(Z)

<400> SEQUENCE: 9

Xaa Arg Pro Ala Lys
 1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ala, Gly, Asn, Arg(Tos), Lys(Z), Arg, or Lys

<400> SEQUENCE: 10

Xaa Arg Pro Ala Lys
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ala, Gly, Gln, Lys(CIZ) or Asn
<220> FEATURE:
<221> NAME/KEY: MOD_RES
<222> LOCATION: (2)
<223> OTHER INFORMATION: Arg(Tos)
<220> FEATURE:
<221> NAME/KEY: MOD_RES
<222> LOCATION: (5)
<223> OTHER INFORMATION: Lys(CIZ)

<400> SEQUENCE: 11

Xaa Arg Pro Ala Lys
 1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Arg(Tos)
<220> FEATURE:
<221> NAME/KEY: MOD_RES
<222> LOCATION: (4)
<223> OTHER INFORMATION: Lys(CIZ)

<400> SEQUENCE: 12

Arg Pro Ala Lys
 1
```

```
<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Arg(Tos)
<220> FEATURE:
<221> NAME/KEY: MOD_RES
<222> LOCATION: (5)
<223> OTHER INFORMATION: Lys(CIZ)

<400> SEQUENCE: 13

Ala Arg Pro Ala Lys
 1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Arg(Tos)
<220> FEATURE:
<221> NAME/KEY: MOD_RES
<222> LOCATION: (5)
<223> OTHER INFORMATION: Lys(CIZ)

<400> SEQUENCE: 14

Gly Arg Pro Ala Lys
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(CIZ)
<220> FEATURE:
<221> NAME/KEY: MOD_RES
<222> LOCATION: (2)
<223> OTHER INFORMATION: Arg(Tos)
<220> FEATURE:
<221> NAME/KEY: MOD_RES
<222> LOCATION: (5)
<223> OTHER INFORMATION: Lys(CIZ)

<400> SEQUENCE: 15

Lys Arg Pro Ala Lys
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)
<223> OTHER INFORMATION: Arg(Tos)
<220> FEATURE:
<221> NAME/KEY: MOD_RES
<222> LOCATION: (5)
<223> OTHER INFORMATION: Lys(CIZ)

<400> SEQUENCE: 16

Gln Arg Pro Ala Lys
 1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Arg(Tos)
<220> FEATURE:
<221> NAME/KEY: MOD_RES
<222> LOCATION: (5)
<223> OTHER INFORMATION: Lys(CIZ)

<400> SEQUENCE: 17

Asn Arg Pro Ala Lys
 1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Arg(Tos)
<220> FEATURE:
<221> NAME/KEY: MOD_RES
<222> LOCATION: (2)
<223> OTHER INFORMATION: Arg(Tos)
<220> FEATURE:
<221> NAME/KEY: MOD_RES
<222> LOCATION: (5)
<223> OTHER INFORMATION: Lys(CIZ)

<400> SEQUENCE: 18

Arg Arg Pro Ala Lys
 1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Arg Pro Ala Lys
 1               5

<210> SEQ ID NO 20
<211> LENGTH: 5
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 20

Arg Arg Pro Ala Lys
  1               5
```